US012559364B2

(12) United States Patent
Rajaraman et al.

(10) Patent No.: US 12,559,364 B2
(45) Date of Patent: Feb. 24, 2026

(54) 3D MICROELECTRODE ARRAY (MEA) FOR OPTICAL AND ELECTRICAL PROBING OF ELECTROGENIC CELLS

(71) Applicants: UNIVERSITY OF CENTRAL FLORIDA RESEARCH FOUNDATION, INC., Orlando, FL (US); AXOSIM, Inc., New Orleans, LA (US)

(72) Inventors: Swaminathan Rajaraman, Winter Park, FL (US); Charles M. Didier, Orlando, FL (US); Avra Kundu, Orlando, FL (US); Lowry Curley, New Orleans, LA (US); Michael J. Moore, New Orleans, LA (US); Hieu Nguyen, New Orleans, LA (US); Corey Rountree, New Orleans, LA (US)

(73) Assignees: UNIVERSITY OF CENTRAL FLORIDA RESEARCH FOUNDATION, INC., Orlando, FL (US); AXOSIM, Inc., New Orleans, LA (US)

( * ) Notice: Subject to any disclaimer, the term of this patent is extended or adjusted under 35 U.S.C. 154(b) by 774 days.

(21) Appl. No.: 17/777,162

(22) PCT Filed: Nov. 16, 2020

(86) PCT No.: PCT/US2020/060779
§ 371 (c)(1),
(2) Date: May 16, 2022

(87) PCT Pub. No.: WO2021/097447
PCT Pub. Date: May 20, 2021

(65) Prior Publication Data
US 2022/0402755 A1    Dec. 22, 2022

Related U.S. Application Data

(60) Provisional application No. 63/083,976, filed on Sep. 27, 2020, provisional application No. 62/935,987, filed on Nov. 15, 2019.

(51) Int. Cl.
*B81C 1/00* (2006.01)
*B01L 3/00* (2006.01)
(Continued)

(52) U.S. Cl.
CPC ..... *B81C 1/00111* (2013.01); *B01L 3/502707* (2013.01); *B81B 1/008* (2013.01);
(Continued)

(58) Field of Classification Search
CPC ........ A61B 2562/028; A61B 2562/125; A61B 5/262; A61B 5/283; A61B 5/388;
(Continued)

(56) References Cited

U.S. PATENT DOCUMENTS 7,682,816 B2    3/2010  Kim et al.
9,302,903 B2 *  4/2016  Park ................ A61B 5/150984
(Continued)

FOREIGN PATENT DOCUMENTS

WO      2018191556 A1    10/2018
WO      2021079447 A1    5/2021

OTHER PUBLICATIONS

Axion BioSystems, "See What Cells Can Do", Axion BioSystems, Inc., 2022, 2 pages.
(Continued)

*Primary Examiner* — Jennifer Wecker
(74) *Attorney, Agent, or Firm* — Timothy H. Van Dyke; Wolter Van Dyke Davis, PLLC

(57) ABSTRACT

Disclosed herein are novel 3D microelectrode arrays (3D MEA) that include a substrate body (e.g. chip),
(Continued)

microneedles, traces, and a well, wherein the 3D MEA provides for transfer of electrical signals on one side of the substrate body to the other side of the substrate body. Methods for using 3D MEAs to grow electrogenic cells and obtain electrophysiological signals are disclosed as well. Fabrication techniques for producing the 3D MEAs are also disclosed.

20 Claims, 11 Drawing Sheets

(51) Int. Cl.
  *B81B 1/00* (2006.01)
  *G01N 33/487* (2006.01)
(52) U.S. Cl.
  CPC *G01N 33/48728* (2013.01); *B01L 2300/0645* (2013.01); *B01L 2300/0654* (2013.01); *B01L 2300/0819* (2013.01); *B81B 2201/055* (2013.01)
(58) Field of Classification Search
  CPC .......... G01N 33/48728; B81C 1/00111; B81B 1/008; B81B 2201/055; B01L 2300/0645; B01L 2300/0654; B01L 2300/0819; B01L 3/502707; A61N 1/05
  See application file for complete search history.

(56) References Cited

U.S. PATENT DOCUMENTS

| | | | | |
|---|---|---|---|---|
| 12,174,140 B2 * | 12/2024 | Ham | .................... | A61N 1/0551 |
| 2011/0125001 A1 | 5/2011 | Fang et al. | | |
| 2014/0303471 A1 | 10/2014 | Rajaraman et al. | | |
| 2014/0336487 A1 * | 11/2014 | Wang | .................... | A61B 5/6833 |
| | | | | 600/352 |
| 2015/0027885 A1 * | 1/2015 | Rajaraman | ......... | G01N 33/4836 |
| | | | | 204/403.13 |
| 2016/0017268 A1 | 1/2016 | Kim et al. | | |
| 2017/0007813 A1 | 1/2017 | Negi et al. | | |
| 2017/0276668 A1 | 9/2017 | Curley et al. | | |
| 2019/0240658 A1 | 8/2019 | Rajaraman et al. | | |

OTHER PUBLICATIONS

Azim, Nilab et al., "Fabrication and Characterization of a 3D Printed, MicroElectrodes Platform With Functionalized Electrospun Nano-Scaffolds and Spin Coated 3D Insulatation Towards Multi-Functional Biosystems", Journal of Microelectromechanical Systems, IEEE, 2019, 13 pages.
Azim, Nilab et al., "Precision Plating of Human Electrogenic Cells on Microelectrodes Enhanced With Precision Electrodeposited Nano-Porous Platinum for Cell-Based Biosensing Applications", Journal of Microelectromechanical Systems, Feb. 1, 2019, vol. 28, No. 1.
Borkholder, David A. "Cell Based Biosensors Using Microelectrodes", A Dissertation, Nov. 1998, 254 pages.
Brug, G.J. et al., "The Analysis of Electrode Impedances Complicated by the Presence of a Constant Phase Element", J. Electroanal Chem, 1984, vol. 176, pp. 275-295.
Busek, David et al., "Study of Glass Transition Temperature of Electrically Conductive Adhesives", IEEE, Oct. 25-28, 2012, 4 pages.

Claycomb, William C. et al., "HL-1 cells: A cardiac muscle cell line that contracts and retains phenotypic characteristics of adult cardiomyocyte", Proc. Natl. Acad. Sci. USA, Mar. 1998, vol. 95, pp. 2979-2984.
Didier, Charles M. et al., "Facile, Packaging Substrate-Agnostic, Microfabrication and Assembly of Scalable 3D Metal Microelectrode Arrays for in Vitro Organ-On-A-Chip and Cellular Disease Modeling", IEEE, Jun. 23-27, 2019, Eurosensors, pp. 1686-1689.
Didier, Charles M. et al., "Fabrication and Characterization of 3D Microelectrode Arrays (3D Meas) With "Edge-wrapped" Metal Interconnects and Electrical Probing of Nerve-On-A-Chip Constructs", 2021 IEEE 34th International Conference on Micro Electro Mechanical Systems (MEMS), 2021, pp. 226-229.
Egert, Ulrich et al., "Heart on a Chip—Extracellular Multielectrode Recordings from Cardiac Myocytes in Vitro", In-Vitro Techniques, Jan. 2005, vol. 3, No. 10, pp. 432-453.
Guvanasen, Gareth S. et al., "A stretchable microneedle electrode array for stimulating and measuring intramuscular electromyographic activity", IEEE Transactions on Neural Systems and Rehabilitation Engineering, Sep. 2017, vol. 25, No. 9, pp. 1440-1452.
Harrington, David A. et al., "Mechanism and equivalent circuits in electrochemical impedance spectroscopy", Electrochim. Acta, Jan. 17, 2011, vol. 56, pp. 8005-8013.
Hong, Jin Hee et al., "Spiral reentry waves in confluent layer of HL-1 cardiomyocyte cell lines", Biochemical and Biophysical Research Communications, 2008, vol. 377, pp. 1269-1273.
Jeong, Sehoon et al., "A three-dimensional arrayed microfluidic blood-brain barrier model with integrated electrical sensor array", IEEE Transactions on Biomedical Engineering, Feb. 2018, vol. 65, No. 2, pp. 431-439.
Karnati, Chandana et al., "Micromachining on and of Transparent Polymers for Patterning Electrodes and Growing Electrically Active Cells for Buisensor Applications", Micromachines, 2017, vol. 8, No. 250, 22 pages.
Kim, Geon Hwee et al., "Recent Progress on Microelectrodes in Neural Interfaces", Materials, 2018, vol. 11, No. 1995, 25 pages.
Kundu, Avra et al., "Optimaization of makerspace microfabrication techniques and materials for the realization of planar, 3D printed microelectrode arrays in under four days", RSC Adv., 2019, vol. 9, pp. 8949-8963.
Kundu, Avra et al., "3D Printing, Ink Casting and Micromachined Lamination (3D PICLuM): A Makerspace Approach to the Fabrication of Biological Microdevices", Micromachines, 2018, vol. 9, No. 85, 23 pages.
Lacroix, C. et al., "Properties of PETG/EVA blends: 1. Viscoelastic, morphological and interfacial properties", Polymer, 1996, vol. 37, No. 14, pp. 2939-2947.
Muse Adapter Manual, NanoBioSensors & Systems Group, V2019-07-10, 2019, 4 pages.
Pollard, Kevin J., "Neural microphysiological systems for <i> in vitro </i? modeling of peripheral nervous system disorder", Biolectronics in Medicine, Jun. 2019, vol. 2, issue 2, pp. 101-117.
Prado, J. et al., "Bioimpedance spectroscopy of human blood at low frequency using coplanar microelectrodes", Medicon 2007, IFMBE Proceedings 16, pp. 186-189, 2007.
Sharma, Anup D. et al., "Engineering a 3D functional human peripheral nerve in vitro using the Nerve-on-a-Chip platform", Scientific Reports, 2019, vol. 9, vol. 8921, 12 pages.
Viswan, Vijay et al., "Optimal Electrode Size for Multi-Scale Extracellular-Potential Recording from Neuronal Assemblies", Frontiers in Neuroscience, Apr. 26, 2019, vol. 13, article 385, 23 pages.
Watt, Fiona M. et al., "Role of the extracellular matrix in regulating stem cell fate", Nature Reviews | Molecular Cell Biology, Aug. 2013, vol. 14, pp. 467-473.
JP Search report, Ref. No. J7141 Dispatch No. 000869 Dispatch Date: Jan. 14, 2025, 8 pages.

* cited by examiner

3D MICROELECTRODE ARRAY (MEA) FOR OPTICAL AND ELECTRICAL PROBING OF ELECTROGENIC CELLS

CROSS REFERENCE TO RELATED APPLICATIONS

This application claims the benefit of U.S. Provisional Application No. 62/935,987 filed Nov. 15, 2019, and U.S. Provisional Application No. 62/083,976 filed Sep. 27, 2020, the entire contents of which are incorporated herein by reference in their entirety.

STATEMENT REGARDING FEDERALLY SPONSORED RESEARCH

Government Support Clause

This invention was made with government support under NSF REU grant number NSF-EEC 1560007 awarded by the National Science Foundation; NSF IUCRC MIST Center grant number NSF-IIP 1439680 awarded by the National Science Foundation; and SBIR funding 1R43 ES029886-01 awarded by the National Institutes of Health. The government has certain rights in the invention.

All patents, patent applications, and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND

Microelectrode array (MEA) fabrication is vital to many fields that require a reliable device for interfacing between electronic circuits and biological cells such as neurons and cardiomyocytes in vitro. MEAs along with cells allow for prediction of a drug's behavior prior to clinical trials and evades numerous, expensive late stage drug development failures and market withdrawals. MEAs are used to monitor the electrical signals emanating from electrogenic cells or to stimulate these cells electrically. These measurements are made in real-time, allowing researchers to study how a cluster of cells reacts in a small network area in vitro in the vicinity of the microelectrode with great accuracy. The utilization of MEAs decreases the need for animals in toxicity tests and allows for better benchtop drug screening prior to animal studies or human clinical trials. As a result, MEAs today are used in "disease-on-a-chip" models for neural diseases such as Parkinson's, epilepsy, Amyotrophic Lateral Sclerosis (ALS), neuropathic pain and autism spectrum disorders. Additionally, it may also be used to improve the existing cardiac safety mechanisms to evaluate arrhythmia risk. MEA technology can therefore advance disease modeling, drug discovery, safety and toxicology.

The traditional requirement for clean rooms and specialized skills has inhibited many biologists from pursuing new microfluidic innovations. Makerspaces provide a growing alternative to clean rooms: they provide low-cost access to fabrication equipment such as laser cutters, plotter cutters, and 3D printers; use commercially available materials; and attract a diverse community of product designers. In the broadest sense, makerspaces are physical spaces, usually accessible to the public, where communities are able to access tools—spanning additive and subtractive techniques—for fabricating "almost anything." Such spaces can be formalized as part of an organization like the Fab Lab network (fabfoundation.org), or more informally organized. With over one thousand active spaces around the world, makerspaces have lowered the barrier to accessing fabrication technologies, enabling the exploration of microfluidic rapid prototyping techniques.

A key factor in the shift of microfluidic manufacturing from traditional photolithographic methods to 'maker manufacturing' is the push for fully integrated microfluidic systems that can be readily translated to industry. However, a major roadblock for lab-on-a-chip devices is plugging and sealing the device to all the interfaces needed (e.g., detection, electric manipulation, and inlets/outlets).

BRIEF DESCRIPTION OF THE DRAWINGS

(FIG. 1A) Laser micromachining a Washington Tower geometry using 1064 nm (IR) wavelength using Quick Laze 50ST2, Eolite Lasers onto a stainless steel substrate having a thickness of 25 μm. (FIG. 1B) Transitioning the laser micromachined area out-of-plane using a hypodermic needle and releasing the 3D microneedles from the stainless steel substrate by laser micromachining at the same wavelength, 1064 nm (IR). (FIG. 1C) The key-shape of the released 3D microneedles. The microneedles have a width of 300 μm, height of 400 μm and a pitch of 600 μm. The key-shaped cutout obtained in the stainless steel sheet shown as inset.

(FIG. 2A) Glass chip (500 μm thickness) cleaned in ~2 M solution of KOH (potassium hydroxide) in IPA (isopropyl alcohol; 2-propanol). (FIG. 2B) Metallization of a stack of Titanium-Gold (30 nm-90 nm) using electron beam evaporation through a Kapton shadow mask. The Kapton shadow mask was laser micromachined using 355 nm (UV). (FIG. 2C) The Titanium-Gold traces are 150 μm wide and the contact pads are designed to be 1 mm×1 mm (FIG. 2D) The 3D microneedles are aligned with the traces and bonded using silver paste. As noted above, other suitable materials can be used including gold, graphene or carbon nanotubes. The silver paste can be cast through the SS cutout. (FIG. 2E) The glass chip bonded using silver paste with the 3D stainless steel key-shape having 10 microneedles. (FIG. 2F) A PET-G culture ring is attached using PDMS and the 3D microneedles are isolated from each other using laser micromachining (1064 nm) to yield 10 numbers of 3D recording/stimulating sites. (FIG. 2G) Controlled precision drop-casting and self-planarization of PDMS to achieve the insulation layer. (FIG. 2H) The volume of PDMS controls the height of the PDMS insulation in the area confined by the PET-G ring and determines the geometric area of the 3D Microelectrode Array (MEA). (FIG. 2I) HL-1 cells interacting with a singular 3D MEA.

(FIG. 3A) Affixing a 3D printed frame printed in Asiga MAX 27UV. Two frames slide onto each side of the glass. The frames have a designed groove of 700 μm into which the glass chip slides. The diameter of the vias is 1 mm and the channel which transitions the vias to the bottom side of the frame is 1 mm wide. (FIG. 3B) Silver ink casting of the 3D printed vias effectively transitions the gold pads on the top side of the glass chip to silver pads on the bottom side of the 3D printed frame.

(FIG. 4C) Box plot of the angle of tilt for the 3D microneedles transitioned out-of-plane after laser micromachining (N=10). (FIG. 4D) SEM image of the laser scribed key-shaped array to define 10 individual 3D microneedles. A close-up SEM image shows the laser scribe lines and the 3D microneedle resting on a layer of silver paste. (FIG. 4E) SEM image of the PDMS insulated 3D MEAs. PDMS insulates the traces and the planar portions of the device to yield the recording/stimulating sites at a height of ~400 µm. (FIG. 4F) Close-up of a singular 3D MEA is shown as an inset.

(FIG. 5A) Glass chip with T-Au metal traces and pads. (FIG. 5B) Microphotograph of the device after the 3D microneedles are bonded to the glass substrate using silver paste and subsequently laser micromachined to be isolated from each other as seen in (FIG. 5C). (FIG. 5D) Fully assembled device with the 3D printed frame slid onto the glass chip. (FIG. 5E) Close up image of the 3D printed via showing the metallized gold pad aligned with the vias on the 3D printed frame. (FIG. 5F) Ready-to-interface device with the vias filled with silver paste so that the gold traces on the top side of the glass chip transitions to the bottom face of the packaged device.

(FIG. 6A) Impedance (Real) spectra of the assembled device, packaged device with 3D printed frame and fitted plot as per Randles equivalent circuit. (FIG. 6B) Phase spectra of the assembled device, packaged device with 3D printed frame and fitted plot as per (FIG. 6C) Randles' equivalent circuit used for circuit fitting and extraction. (FIG. 6D) Box plot of the DC resistance of the via after silver ink casting (FIG. 7C) Noise plot of 3D MEA, (FIG. 7D) Optical microphotograph of HL-1 cells after 2 DIV (FIG. 7E) Axion Biosystems MUSE Cardiac Beat from HL-1 cells and (FIG. 7F) Exaggerated plot of a single beat from HL-1 Cardiac beat.

FIG. 8(A) (i) Schematic rendering for the 10-microelectrode key-shaped array configuration (IR laser denoted in red). (ii) Optical image of the laser micromachined 2D key-shaped array with relief cuts. FIG. 8(B) (i) Schematic rendering of the 3D printed transition structure. (ii) SEM image of the printed transition structure. FIG. 8(C) (i) Schematic rendering of the final key-shaped MEA, with all 10 microelectrodes transitioned to vertical 3D state. (ii) SEM image of the application of the 3D printed transition rig pushing acid pickled microelectrodes to their final 3D MEA state. The inset shows a closer SEM of a SS microelectrode tip. FIG. 8(D) (i) Schematic process flow for the "edge-wrapped" metallization and culture well assembly for the 3D MEA. (i) UV laser definition of the Kapton® mask pattern. (ii) The mask is wrapped around the glass substrate to cover the edge and the back of the substrate, and then is placed on the angular deposition rig. (iii) Traces are deposited through an e-beam deposition process. (iv) After removal of the mask, the key-shaped MEA is attached atop the traces using a conductive ink-epoxy, and the device is cured. (v) The electrodes are then selectively isolated using IR laser micromachining (vi) A PETG culture well is then attached with PDMS. The insulation is defined with precision drop casting of PDMS and curing. FIG. 8(E) (i) Optical image of the fabricated device on the Axion BioSystems MUSE system. (ii) Close up of the tissue culturing area.

FIG. 10(A) Full frequency spectrum impedance of the MEA platform (N=4). At the physiologically relevant 1 kHz real part of the impedance is 7.5 kΩ, and phase is −20° both values in the expected range for microelectrodes. FIG. 10(B) Noise measurements of the 3D MEA platform (N=4). The noise measurements were taken on the Axion BioSystems MUSE platform, outfitted with a custom interfacing module, and recorded with the AxIS software. Screen capture of channels 35, 65, 77, and 87 are shown with RMS noise in PBS of 3.18 µV, 3.64 µV, 3.65 µV, and 3.29 µV respectively. These noise measurements average out to 3.44 µV; within the desired range for stimulating and recording microelectrodes. FIG. 10(C) Angular spread of transitionary rig performance. The 3D printed transition rig reliably sets the needles in the key-shaped conformation at mean of 80° (N=10).

FIG. 11(A) Fluorescent Calcein staining of DRG cells on the key-shaped construct. FIG. 11(B) Brightfield microscopy of the DRGs containing region of the key-shaped construct (outlined in red). FIG. 11(B) Brightfield microscopy the DRG cell body culture, overlaid with the Calcein stain from FIG. 11(A).

DETAILED DESCRIPTION

Figures 1A, 1B, 1C:
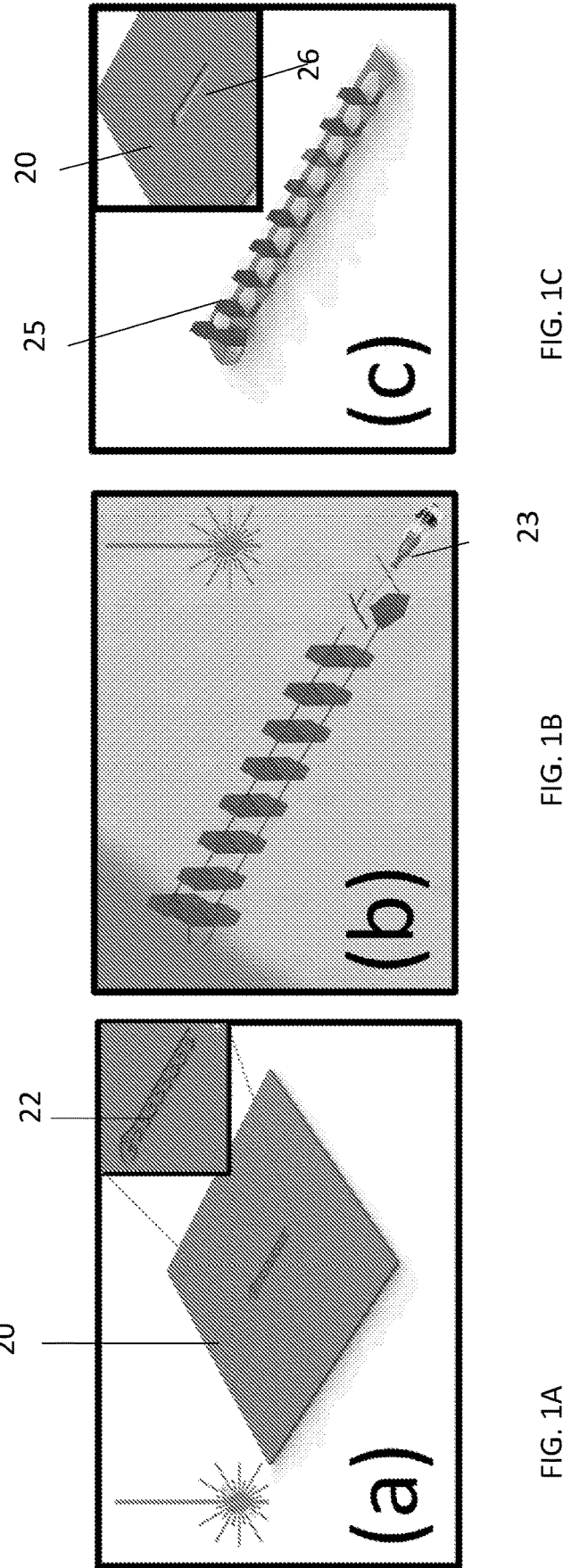
FIGS. 1A-1C show a Schematic Process Flow of laser micromachining.

Disclosed herein is the microfabrication and assembly of a Three-Dimensional Microelectrode Array (3D MEA) based on a glass-stainless steel platform. The presented technique involves the use of non-traditional "Makerspace Microfabrication" techniques which allows cost effective fabrication of the device using an assorted biocompatible material palette in a rapid timeframe.

In one embodiment of a 3D MEA, stainless-steel electrodes having a height of about 400 µm and width of about 300 µm are produced by planar laser micromachining and transitioned out of plane to have a 3D configuration. The 2D to 3D transition angles can be consistently perpendicular to the micromachining plane. The laser micromachined 3D stainless steel electrodes can be bonded onto a glass die with metal traces routed to the edge for the chip for measuring electrophysiological activities from electrogenic cells. Confined precision drop casting (CPDC) of polydimethylsiloxane (PDMS) or other insulation material can be implemented to define a uniform insulation and realize the 3D MEA. In a specific embodiment, glass is used as a substrate material, which offers optical clarity that allows for simultaneous optical and electrical probing from the electrogenic cell culture.

Additionally, a unique interconnect interface using 3D printing and conductive ink casting is disclosed, which allows for the traces to be transitioned to the bottom side of the device for interfacing the fabricated device with commercial data acquisition and analysis equipment. In one embodiment, the 3D MEAs demonstrate an average impedance and phase of ~13.3 kΩ and about −12.1° respectively at an electrophysiological relevant frequency of about 1 kHz. The custom fabricated interconnect which transitions the electrical contact from the top-side of the glass chip to the bottom-side of the device exhibits high electrical conductivity demonstrating its effectiveness as an interconnect for a biological microdevice. Electrophysiological activity from cells (e g immortal cardiomyocyte cells among others) are recorded from the 3D MEA demonstrating end to end development of the device. Such a 3D MEA can be implemented to play a major role in pharmacological screening and electrophysiological evaluation of electrogenic cultures on the benchtop. Note that US Pat. Publ. US20190240658 is incorporated herein in its entirety as background and support information.

In other embodiments, disclosed herein is a microfabrication and assembly strategy to produce 3D MEAs designed for simultaneous optical and electrical probing of microengineered physiological systems, such as a Nerve-on-a-Chip® construct. The microfabrication and assembly process of this embodiment include "edge-wrapped" metal interconnects and custom Digital Light Processing (DLP) 3D printed transition rigs respectively. In one embodiment, a Nerve-on-a-Chip® construct comprising nerve cells (e.g., primary rat Dorsal Root Ganglion (DRG) cells) are further seeded and grown atop the 3D MEA for 28 Days in vitro (DIV). The results surrounding the testing of the fabrication technology are presented herein, as well as Impedance Spectroscopy, Root Mean Square (RMS) noise characterization, mechanical stability of the MEAs and long-term culture viability of the integrated tissue chip (Nerve-on-a-Chip® construct on the 3D MEAs) with fluorescence imaging.

The embodiments described herein have a number of uses and implementations. Examples include but are not limited to the following: toxicity testing, drug screening, safety testing, disease modeling, stem cell evaluation, organ and nerve-on-a-chip models, optical and electrical stimulation of various cell types; agricultural plant system models; environmental and gas sensing, among others.

DEFINITIONS

Detailed descriptions of one or more preferred embodiments are provided herein. It is to be understood, however, that the present invention can be embodied in various forms. Therefore, specific details disclosed herein are not to be interpreted as limiting, but rather as a basis for the claims and as a representative basis for teaching one skilled in the art to employ the present invention in any appropriate manner.

The singular forms "a," "an," and "the" include plural reference unless the context clearly dictates otherwise. The use of the word "a" or "an" when used in conjunction with the term "comprising" in the claims and/or the specification can refer to "one," but can also refer to "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

The terms "comprising" and "including" and "having" and "involving" (and similarly "comprises," "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" can refer to "approximately," "roughly," "around," or "in the region of." When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower). As used herein, the terms "microengineered physiological system," "organotypic preparations," "3D cellular networks," "3D organ model" "organs-on-a-chip," and the like can refer to any biomimetic in vitro system. In embodiments, the microengineered physiological systems are configured to express structural and functional characteristics of a particular biological system. One example of a microengineered system includes a three-dimensional cell culturing system. In one embodiment, the microengineered physiological system comprises a three-dimensional cell culturing system for neural cells that promotes both structural and functional characteristics that mimic those of in vivo nerve fibers. Certain microengineered physiological systems can be configured to promote the growth of isolated cells, tissue explants, tissue explant fragments, or a combination thereof. In embodiments, the microengineered physiological system includes neuronal cells, neural cells, neural tissue explants, or a combination thereof. In embodiments, the microengineered physiological system comprises any of the various systems disclosed in U.S. patent application Ser. No. 15/510,977, the entire contents of which is hereby incorporated by reference. The microengineered physiological system can comprise any of the various systems disclosed in U.S. patent application Ser. No. 16/077,411, the entire contents of which is hereby incorporated by reference.

As used herein, "tissue explants" can comprise any tissue obtained, isolated, or otherwise disassociated from an organism or subject. Exemplary tissue explants include an isolated neural explant. Tissue explants can comprise an explant of any electrically active or electrically responsive tissue. In embodiments, the tissue explant includes an explant of peripheral neural tissue, and explant of central neural tissue, or a combination thereof. An explant can be a brain-derived tissue explant, a spinal cord-derived tissue explant, an enteric-derived tissue explant, a peripheral-derived tissue explant, or a combination thereof. In embodiments, the tissue explant comprises a dorsal root ganglion (DRG) explant, a, a retinal explant, a cortical explant, or a combination thereof. A tissue explant can comprise a plurality of one or more neuronal cells.

As used herein, "tissue explants" can comprise any tissue obtained, isolated, or otherwise disassociated from an organism or subject. Exemplary tissue explants include an isolated neural explant. Tissue explants can comprise an explant of any electrically active or electrically responsive tissue. In embodiments, the tissue explant includes an explant of peripheral neural tissue, and explant of central neural tissue, or a combination thereof. An explant can be a brain-derived tissue explant, a spinal cord-derived tissue explant, an enteric-derived tissue explant, a peripheral-derived tissue explant, or a combination thereof. In embodiments, the tissue explant comprises a dorsal root ganglion (DRG) explant, a, a retinal explant, a cortical explant, or a combination thereof. A tissue explant can comprise a plurality of one or more neuronal cells.

The terms "neuronal cells," "neural cells," and the like, as used herein can refer to cells that comprise at least one or a combination of dendrites, axons, and somata, or, alternatively, any cell or group of cells isolated from or found within nervous system tissue. In embodiments, neuronal cells are any cell that comprises or is capable of forming an axon. Neuronal cells can comprise isolated primary ganglion tissue. In some embodiments, the neural cell is a Schwann cell, a glial cell, neuroglia, a cortical neuron, an embryonic cell isolated from or derived from neuronal tissue or that has differentiated into a cell with a neuronal phenotype or a phenotype which is substantially similar to a phenotype of a neural cell, induced pluripotent stem cells (iPS) that have differentiated into a neuronal phenotype, or mesenchymal stem cells that are derived from neural tissue or differentiated into a neural phenotype. In certain embodiments, neuronal cells are neurons from dorsal root ganglia (DRG) tissue, retinal tissue, spinal cord tissue, enteric tissue, or brain tissue, in each case from an adult, adolescent, child, or fetal subject. In some embodiments, neural cells are any one or plurality of cells isolated from the neural tissue of a subject. In embodiments, neural cells comprise a primary cell derived from the peripheral nervous system of a subject, a primary cell derived from the central nervous system of a subject, or a combination thereof. In some embodiments, the neural cells are mammalian cells. In embodiments, the cells are human cells. In certain embodiments, the neural cells are derived from primary human tissue or from human stem cells. In some embodiments, the cells are non-human mammalian cells or derived from cells that are isolated from non-human mammals. If isolated or disassociated from the original animal from which the cells are derived, the neuronal cells can comprise isolated neurons from more than one species.

In embodiments, neuronal cells are one or more of the following neurons: sympathetic neurons, spinal motor neurons, central nervous system neurons, motor neurons, sensory neurons, cholinergic neurons, GABAergic neurons, glutamatergic neurons, dopaminergic neurons, serotonergic neurons, interneurons, adrenergic neurons, and trigeminal ganglion neurons. In some embodiments, neural cells are one or more of the following glial cells: astrocytes, oligodendrocytes, Schwann cells, microglia, ependymal cells, radial glia, satellite cells, enteric glial cells, and pituyicytes.

In some embodiments, neural cells are one or more of the following immune cells: macrophages, T cells, B cells, leukocytes, lymphocytes, monocytes, mast cells, neutrophils, natural killer cells, and basophils. In some embodiments, neural cells are one or more of the following stem cells: hematopoietic stem cells, neural stem cells, adipose derived stem cells, bone marrow derived stem cells, induced pluripotent stem cells, astrocyte derived induced pluripotent stem cells, fibroblast derived induced pluripotent stem cells, renal epithelial derived induced pluripotent stem cells, keratinocyte derived induced pluripotent stem cells, peripheral blood derived induced pluripotent stem cells, hepatocyte derived induced pluripotent stem cells, mesenchymal derived induced pluripotent stem cells, neural stem cell derived induced pluripotent stem cells, adipose stem cell derived induced pluripotent stem cells, preadipocyte derived induced pluripotent stem cells, chondrocyte derived induced pluripotent stem cells, and skeletal muscle derived induced pluripotent stem cells. In some embodiments, neural cells are keratinocytes. In some embodiments, neural cells are endothelial cells.

The term "isolated neurons," "isolated neuronal cells," "isolated neural cells," and the like can refer to neural cells that have been removed or disassociated from an organism or culture from which they originally grow. In some embodiments isolated neurons are neurons in suspension. In some embodiments, isolated neurons are a component of a larger mixture of cells including a tissue sample or a suspension with non-neuronal or non-neural cells. In some embodiments, neural cells have become isolated when they are removed from the animal from which they are derived, such as in the case of a tissue explant. In some embodiments isolated neurons are those neurons in a DRG excised from an animal. In some embodiments, the isolated neurons comprise at least one or a plurality cells that are from one species or a combination of the species chosen from: sheep cells, goat cells, horse cells, cow cells, human cells, monkey cells, mouse cells, rat cells, rabbit cells, canine cells, feline cells, porcine cells, or other non-human mammals. In some embodiments, the isolated neurons are human cells. In some embodiments, the isolated neurons are stem cells that are pre-conditioned to have a differentiated phenotype similar to or substantially similar to a human neuronal cell. In some embodiments, the isolated neurons are human cells. In some embodiments, the isolated neurons are stem cells that are pre-conditioned to have a differentiated phenotype similar to or substantially similar to a non-human neuronal cell. In some embodiments, the stem cells are selected from: mesenchymal stem cells, induced pluripotent stem cells, embryonic stem cells, hematopoietic stem cells, epidermal stem cells, stem cells isolated from the umbilical cord of a mammal, or endodermal stem cells.

The terms "neuronal cell culture medium" or simply "culture medium" as used herein can refer to any nutritive substance suitable for supporting the growth, culture, cultivating, proliferating, propagating, or otherwise manipulating of cells. In some embodiments, the medium comprises neurobasal medium supplemented with nerve growth factor (NGF). In some embodiments, the medium comprises fetal bovine serum (FBS). In embodiments, the medium comprises L-glutamine. The culture medium can comprise cyclic adenosine monophosphate (cAMP). In certain embodiments, the medium comprises ascorbic acid in a concentration ranging from about 0.001% weight by volume to about 0.01% weight by volume. In embodiments, the medium comprises ascorbic acid in a concentration ranging from about 0.001% weight by volume to about 0.008% weight by volume. In some embodiments, the medium comprises ascorbic acid in a concentration ranging from about 0.001% weight by volume to about 0.006% weight by volume. The medium can comprise ascorbic acid in a concentration ranging from about 0.001% weight by volume to about 0.004% weight by volume. In some embodiments, the medium comprises ascorbic acid in a concentration ranging from about 0.002% weight by volume to about 0.01% weight by volume. In embodiments, the medium comprises ascorbic acid in a concentration ranging from about 0.003% weight by volume to about 0.01% weight by volume. In certain embodiments, the medium comprises ascorbic acid in a concentration ranging from about 0.004% weight by volume to about 0.01% weight by volume. In embodiments, the medium comprises ascorbic acid in a concentration ranging from about 0.006% weight by volume to about 0.01% weight by volume. The medium can comprise ascorbic acid in a concentration ranging from about 0.008% weight by volume to about 0.01% weight by volume. In some embodiments, the medium comprises ascorbic acid in a concentration ranging from about 0.002% weight by volume to about 0.006% weight by volume. In some embodiments, the medium comprises ascorbic acid in a concentration ranging from about 0.003% weight by volume to about 0.005% weight by volume. In embodiments that incorporate Schwann cell differentiation, the culture medium can comprise ascorbic acid, FBS, cAMP, or a combination thereof.

The term "subject" as used herein includes all members of the animal kingdom including, but not limited to, mammals, reptiles, animals (e.g., cats, dogs, horses, swine, primates, rats, mice, rabbits, etc.) and humans.

The term "electrical stimulation" can refer to a process in which the cells are being exposed to an electrical current of either alternating current (AC) or direct current (DC). The current can be introduced into the solid substrate or applied via the cell culture media or other suitable components of the cell culture system. In some embodiments, the electrical stimulation is provided to the device or system by positioning one or a plurality of microneedles at different positions within the device or system to create a voltage potential across the cell culture vessel. The microneedles are in operable connection with one or a plurality of amplifiers, voltmeters, ammeters, and/or electrochemical systems (such as batteries or electrical generators) by one or a plurality of wires. Such devices and wires create a circuit through which an electrical current is produced and by which an electrical potential is produced across the tissue culture system.

The term "recording" as used herein can refer to measuring the responses of one or more neuronal cells. Such responses can be electro-physiological responses, for example, patch clamp electrophysiological recordings or field potential recordings.

DETAILED DESCRIPTION OF SPECIFIC EMBODIMENTS

According to one embodiment, disclosed is a method of making a three-dimensional microelectrode array (3D MEA). The method may involve making a plurality of microneedles by forming (typically laser micromachining) a plurality of cut-outs onto a planar conductive sheet; transitioning material at the plurality of the cut-outs such that a plurality of microneedles extend orthogonally to the planar conductive sheet; and cutting the planar conductor sheet to release the plurality of microneedles from the planar sheet to produce a released plurality of microneedles. This method embodiment can further comprises securing the released plurality of microneedles to a transparent planar substrate body comprising a top surface, a bottom surface and an edge surface between the top and bottom surfaces. The transparent planar substrate body can comprise conductive traces on the edge surface and the bottom or top surface, or both, and the released plurality of microneedles is secured suprajacent to the conducted traces such that at least one microneedle of the plurality of microneedles and at least one trace of the one or more conductive traces are conductively connected. The planar conductive substrate may be comprised of metal (e.g. stainless steel). The transparent planar substrate body may be comprised of glass or polymer/plastic. Examples of transparent polymers, include but are not limited to Polystyrene, Polycarbonate, Cyclic Olefin Copolymer, PolyEthylene Terephthalate, and the like, or some co-polymer combination thereof.

Unless specified, the term traces broadly includes any conductive material deposited on the substrate body. The term "traces" includes conductive linear traces and pads as is discussed below with respect to FIG. 2.

The words "microneedle" and "microelectrode" are used interchangeably throughout this disclosure and can refer to electrodes used to record from or stimulate electrogenic cells.

According to another embodiment, a method is disclosed that involves making a transparent planar substrate comprising one or more conductive traces on its edge surface. The method involves covering a transparent planar substrate body with a mask, the mask comprising at least one opening, and the transparent planar substrate body comprising a top surface, a bottom surface and at least one edge surface between the top and bottom surfaces, wherein the at least one opening overlaps the edge surface. Upon covering the method involves depositing a conductive material onto the transparent planar substrate body through the at least one opening, wherein the conductive material is deposited onto the edge surface.

In a specific embodiment, depositing is conducted using an E-beam while holding the transparent planar substrate at an angle respective to the E-beam. In an even more specific embodiment, the method involves associating the transparent planar substrate with oblique angle deposition. In one non-limiting example, the oblique angle deposition utilizes an angled deposition rig that comprises a base portion and a bracket portion secured orthogonally to the base portion.

It is noted that while E-beam deposition is the typical method used for depositing traces according to the disclosure, other deposition methods may be used. These include, but are not limited to, Resistive Deposition, Laser Deposition, Screen Printing, Electroplating, and the like.

In a further embodiment, provided is a method of making a three-dimensional microelectrode array (3D MEA) that involves securing a plurality of microneedles to a transparent planar substrate body comprising a top surface, a bottom surface and edge surface between the top and bottom surfaces and which has one or more conductive traces deposited on the bottom or top surface, or both; attaching at least one frame member to the transparent planar substrate, the at least one frame member comprising at least one groove into which the edge surface is inserted and at least one channel defined therein that spans from the top surface to the bottom surface; and depositing a conductive material into the at least one channel such that the conductive material conductively connects with the at least one trace. The microneedles may be formed by the micromachining process described herein.

The method embodiments described herein the plurality of 3D microneedles are interconnected in an assembly comprising a first portion comprising a first set of 3D microneedles and having a first width dimension and a first length dimension, and a second portion comprising a second set of 3D microneedles and having a second width dimension and a second length dimension, wherein the second width dimension is larger than the first width dimension and the first length dimension is larger than the second length dimension, and, optionally, further comprising conductively isolating the plurality of 3D microneedles from each other.

In one embodiment, the method further includes forming a microengineered microphysiological system. The microengineered microphysiological system can be formed by placing neuronal cells over at least a portion of the second portion or seeding tissue explants over at least a portion of the second portion. The method can further include growing axons over at least a portion of the first portion. In embodiments, the method includes performing real-time, detection of one or more bioelectrical signals in the microengineered physiological system. In embodiments, the first plurality of electrodes, the second plurality of electrodes, or both comprise recording electrodes, stimulation electrodes, or a combination thereof.

Embodiments further include detecting bioelectric signals within the microengineered physiological system during formation and optically tracking the microengineered physiological system during formation. The method can include continuing to detect bioelectric signals and continuing to optically track the microengineered physiological system for up to one year.

According to another embodiment, disclosed is a 3D MEA that includes a transparent planar substrate body comprising a top surface, a bottom surface and an edge surface between the top and bottom surfaces; a plurality of conductive traces deposited onto the edge surface and the top surface or bottom surface or both; and a plurality of micromachined 3D microneedles attached to the transparent planar substrate body such that at least one microneedle of the plurality of 3D microneedles is conductively connected to at least one of the plurality of conductive traces, wherein the micromachined 3D microneedles are comprised of stainless steel.

Another embodiment pertains to a 3D MEA having a transparent planar substrate body comprising a top surface, a bottom surface and an edge surface between the top and bottom surfaces; a plurality of conductive traces disposed upon the transparent planar substrate body; a plurality of micromachined 3D microneedles attached to the transparent planar substrate body such that at least one microneedle of the plurality of 3D microneedles is conductively connected to at least one of the plurality of conductive traces, wherein the micromachined 3D microneedles are comprised of stainless steel; and optionally, at least one frame member associated with the transparent planar substrate body, the at least one frame member comprising at least one groove into which the edge surface is inserted and at least one channel defined therein that spans from the top surface to the bottom surface and a conductive material disposed within the at least one channel so as to provide a conductive connection with at least one of the plurality of conductive traces.

In yet a further embodiment, provided is a 3D MEA comprising a transparent planar substrate body comprising a top surface, a bottom surface and an edge surface between the top and bottom surfaces; a plurality of conductive traces deposited onto the edge surface, the top surface or bottom surface, or a combination thereof; and a plurality of micromachined 3D microneedles attached to the transparent planar substrate body such that at least one microneedle of the plurality of 3D microneedles is conductively connected to at least one of the plurality of conductive traces. The plurality of micromachined 3D microneedles are provided in an assembly comprising a first portion comprising a first set of 3D microneedles and having a first width dimension and a first length dimension, and a second portion comprising a second set of 3D microneedles and having a second width dimension and a second length dimension, wherein the second width dimension is larger than the first width dimension and the first length dimension is larger than the second length dimension. The plurality of micromachined 3D microneedles may be conductively isolated from each other following attachment. In a specific embodiment, the first set comprises about eight 3D microelectrodes and the second set comprises about two 3D microelectrodes. In another specific embodiment, the first width dimension is about 10-500 µm and the first length dimension is about 10-500 µm and the second width dimension is about 10-500 µm and the second length dimension is about 10-500 µm, taking into account that the first length is larger than the second length dimension and the second width dimension is larger than the first width dimension. In one specific example, the first portion and second portion form a geometry wherein the first portion aligns with a neural tract of a nerve cell and the second portion aligns with a ganglion of the nerve cell.

In embodiments, the defined intervals between microneedles within the axonal growth region comprise up to about 5 cm intervals. In embodiments, the defined intervals are up to about 1 cm, about 2 cm, about 3 cm, about 4 cm, or about 5 cm. The defined intervals can be less than 1 cm. In embodiments, the defined intervals are as large as about 9 mm. The defined intervals can be about 1 mm, about 2 mm, about 3 mm, about 4 mm, about 5 mm, about 6 mm, about 7 mm, about 8 mm or about 9 mm. In certain embodiments, the defined intervals between microneedles are less than 1 mm. In some embodiments, the defined intervals comprise between about 100 µm to about 900 µm. In embodiments, the defined intervals are less than 100 µm. The defined intervals between microneedles can be about 10 µm, about 20 µm, about 30 µm, about 50 µm, about 60 µm, about 70 µm, about 80 µm, about 90 µm, or about 100 µm. The defined intervals can be less than about 10 µm. In certain embodiments, the defined intervals comprise a distance of between about 10 µm to about 5 mm. The defined intervals can be between about 100 µm to about 1 mm.

In embodiments, 3D MEA is configured to provide real-time, reliable detection of one or more bioelectrical signals in a microengineered physiological system. The microengineered physiological system can comprises a tissue explant, a suspension of cells, or a combination thereof. In embodiments, the microengineered physiological system comprises neural cells cultured on a micropatterned platform or tissue explants seeded on a micropatterned platform. The micropatterned platform can be configured to permit the formation of a neural architecture that comprises an axonal growth region, a ganglion region, a dendritic region, a synaptic region, a spheroid region, or a combination thereof.

In embodiments, the second portion of the plurality of micromachined 3D microneedles is positioned in the ganglion region or spheroid region. The first portion of the plurality of micromachined 3D microneedles can comprise a plurality of microneedles positioned at defined intervals down the axonal growth region.

In embodiments, the first set of 3D microneedles, the second set of 3D microneedles, or both comprise recording electrodes, stimulation electrodes, or a combination thereof. The defined intervals can comprise up to about 50 μm intervals. In various embodiments, the microelectrode array is configured to detect one or more bioelectric signals in the microengineered physiological system for up to one year. The microelectrode array can be configured to detect one or more bioelectric signals in the microengineered physiological system for up to about eight weeks. In embodiments, the 3D MEA is configured to permit simultaneous electrophysiological and optical tracking of the microengineered physiological system during maturation of the microengineered physiological system.

Another aspect includes a system for reproducibly detecting compound action potentials in microengineered physiological system, the system comprising any of the various 3D MEA disclosed herein, wherein the microengineered physiological system comprises one or more neuronal cells.

When micromachining or micromilling the microneedles and transitioning them from 2D to 3D, the resulting angle can be at a greater than 60, 70 or 80 degree angle respective to the planar conductive sheet. In a specific embodiment the angle is 45-90 degrees, 60-90 degrees, 75-90 degrees or 80-90 degrees. In a more specific embodiment, the microneedles are at a greater than 80 degree angle. An individual microneedle of a plurality of three-dimensional microneedles can comprise a height of up to about 1000 μm. The three-dimensional microneedle can comprise a height of between about 30 μm to about 1000 μm. The three-dimensional microneedle can comprise a height of up to about 800 μm. In embodiments, the height of the three-dimensional microneedle is between about 100 μm to about 500 μm, inclusive. The height of the three-dimensional microneedle can be between about 250 μm to about 450 μm, inclusive. In certain embodiments, the height of the three-dimensional microneedle can be between about 350 μm and 450 μm, inclusive. In embodiments, the three-dimensional microneedle comprises a height of up to about 150 μm. In certain embodiments, the three-dimensional microneedle comprises a height of between about 50 μm to about 150 μm. The three-dimensional microneedle can comprise a height of about 800, 700 μm, 600 μm, 500 μm, 400 μm, 300 μm, 200 μm, or 100 μm. In certain embodiments, the height of the three-dimensional microneedle is about 450 μm. The height of the three-dimensional microneedle can be less than 100 μm. In embodiments, the height of the three-dimensional microneedle is about 100 μm, about 90 μm, about 80 μm, about 70 μm, about 60 μm, about 50 μm, about 40 μm, about 30 μm, about 20 μm, or about 10 μm.

The method embodiments described above may further involve deposing an insulation layer onto the plurality of microneedles before or after they are secured to the transparent planar substrate body. In a specific embodiment, the insulation layer is deposed such that a portion of the plurality of microelectrodes is exposed and a portion of the microelectrodes is covered by the insulation layer. Standard insulation materials may be used for deposing an insulation layer, such as parylene, poly-di-methyl-siloxane (PDMS), SU-8, silicon dioxide, polyimide, polyurethane, poly lactic acid, poly glycolic acid, poly lactic glycolic acid, poly vinyl alcohol, polystyrene, poly ethylene glycol, poly ethylene terephthalate, poly ethylene terephthalate glycol, poly ethylene naphthalate, or a combination thereof. One specific example of insulation materials includes polydimethylsiloxane (PDMS). The insulation layer may be deposed by processes that will be apparent to those skilled in the art in view of the teachings herein. In a specific example, the insulation layer is deposed by confined precision drop casting.

The 3D MEA embodiments described herein may further include cells that are placed onto the plurality of microneedles. This may occur before or after the microneedles are secured to the transparent planar substrate body. In a specific embodiment, the cells are electrogenic cells. Electrophysiological signals may be obtained from the electrogenic cells that are deposed atop the one more microneedles, which is transferred through the conductive connectivity of the one or more microneedles and traces. Electrophysiological signals include voltage changes and electric current produced from the electrogenic cells. Further information about the types of cells that may be implemented and types of electrical measurements is provided below.

The 3D MEA embodiments described herein may further comprise a culture well associated with the transparent planar substrate body such that a liquid solution may be contained overtop of the plurality of microneedles. In related method embodiments of making 3D MEA further comprises associating a culture well with the transparent planar substrate. For example, this would occur after deposing the insulation layer, but not necessarily.

Also, reference is made to a transparent planar substrate which allows for application and/or application of light for observing or monitoring the cells are the cell responses to stimuli. In alternative embodiments, description of the transparent planar substrate with respect to method or 3D MEA embodiments may be substituted with a non-transparent substrate, such as when visual monitoring of cells is not needed or desired.

Cells and Electrophysiological Signal Detection

3D MEAs such as those described herein may be used with any suitable type of cell. For example, the cell may be a prokaryotic cell or a eukaryotic cell. The cell may be from a single-celled organism or a multi-celled organism. In some cases, the cell is genetically engineered, e.g., the cell may be a chimeric cell. The cell may be bacteria, fungi, a plant cell, an animal cell, etc. The cell may be from a human or a non-human animal or mammal (e.g., mouse, rat, pig, etc.). For instance, if the cell is from an animal, the cell may be a cardiac cell, a neural cell (e.g., a cortical neuron, an olfactory receptor neuron, an olfactory sensory neuron, etc.), an osteocyte, an osteoblast, a muscle cell (e.g., a cardiomyocyte), etc. The cell may be a primary cell or an immortalized cell. In some cases, the cell is a primary mammalian neuron (e.g., human cortical neuron, rat cortical neuron, etc.).

In addition, it should be noted that in some embodiments, the cells may be cultured on the 3D MEA using any suitable cell culturing technique. For example, mammalian cells may be cultured at 37° C. in the presence of appropriate cell media.

In yet another aspect, cells, such as neurons, are positioned in electrical communication with one or more microneedles, e.g., as discussed herein. The electrodes may be used to stimulate the cells, and/or determine an electrical condition of the cells. More than one microneedle may be positioned in electrical communication with the cell, for example, in distinct regions of the cell. In some cases, the microneedles may be positioned such that they are relatively close together, for example, spaced apart by no more than about 500 nm. In one embodiment, the microneedles are spaced up to about 1000 nm apart. The microneedles can be spaced less than about 500 nm apart. In embodiments, the microneedles are spaced between 50 nm and 300 nm. The microneedles can be spaced up to about 200 nm apart. In certain embodiments, the microneedles are spaced up to about 500 μm apart. The microneedles can be spaced up to about 1000 μm apart. In certain embodiments, the microneedles are spaced between about 10 μm to about 100 μm apart. The microneedles can be spaced about 25 μm to about 75 μm apart from one another. In one embodiment, the microneedles are about 50 μm apart from one another.

Any cell can be used which exhibits electrical behavior, such as membrane potential. For instance, the cell may be a cell in which it is desired to measure the membrane potential (e.g., instantaneously, as a function of time, in response to an external stimulus, such as a drug or an applied external electrical potential, etc.), the cell may be a cell which can be used to detect electric fields (for example, cells from the ampullae of Lorenzini, which is present in certain types of organisms such as sharks), or the cell may be a cell that can produce an electrical signal, for example, a neuron (which is able to produce an action potential), a cardiomyocyte, or an electrocyte (which is used in organisms such as electric eels or electric ray to produce an electrical discharge). In some cases, a neuron comprises one or more ion channels (e.g., a voltage-gated ion channel, a ligand-gated ion channel). In certain cases, the ligand-gated ion channel of a neuron is a cholinergic receptor (e.g., a protein that responds to the binding of acetylcholine). The cholinergic receptor may, in some cases, belong to the family of neuronal nicotinic acetylcholine receptors (nAchRs). Neuronal nicotinic acetylcholine receptors, which are typically pentameric complexes comprising different combinations of alpha (e.g., α2-α10) and beta (e.g., β3, β4, β5) subunits, may be a potential drug target for neurological disorders such as Parkinson's disease, Alzheimer's, and/or hyperactivity disorders.

The microneedle(s) may be in electrical communication with a portion of the cell, i.e., the microneedle may be positioned, relative to the cell, such that the microneedle is able to determine or affect the electrical behavior of the cell, and/or of a region of the cell. The microneedles may be of dimensions such that the microneedle can be used to measure or determine a distinct region of a cell. As a non-limiting example, if the cell is a neuron, the microneedle may be positioned such that the microneedle is able to determine or affect the electrical behavior of a portion of the axon, dendrite, and/or soma of the neuron. The microneedle may be in physical contact with the cell, or not in physical contact but positioned such that changes in the electrical state of the cell are able to affect the electrical state of the microneedle, and/or vice versa. In some embodiments, at least a portion of the microneedle is inserted in the cell. As noted throughout, one or more than one microneedle may be in electrical communication with the cell.

In one set of embodiments, a cell in electrical communication with a microneedle can be electrically stimulated by passing a current or applying a potential to the microneedle, which may be used to affect the electrical state of the cell. For example, the membrane potential of a cell may be altered upon electrical stimulation, or a neuron can be stimulated to cause the neuron to polarize (e.g., hyperpolarize) or depolarize upon the application of sufficient current or potential. In some cases, a current or potential may be applied to the electrode by a stimulator unit.

In another set of embodiments, a change in an electrical state of a cell, such as cell polarization or depolarization, an action potential, a change in plasma membrane potential (e.g., a postsynaptic potential), or the like may cause a change in the electrical state of an microneedle in electrical communication with the cell, such as a change in conductance, which change can be determined and/or recorded in some fashion, e.g., using techniques known to those of ordinary skill in the art. In some cases, the change in electrical state (e.g., an electrical signal) may be stored (e.g., in digital memory), output to a display, and/or modified/converted in some manner. Accordingly, one embodiment of the invention provides for the determination of an electrical state of a cell using a microneedle as described herein. According to some embodiments, at least a portion of the microneedle is inserted in the cell (e.g., in the intracellular space). In some cases, an electrical signal may be transmitted from the cell to the microneedle, and the signal may subsequently be transmitted to an amplifier unit in electrical communication with the microneedle. In some cases, the cell may also be one which was electrically stimulated, e.g., electrically stimulated by applying current or a potential to an microneedle that is in electrical communication with the cell. As a specific example, the electrical state of a neuron, or a portion thereof (e.g., an axon, a dendrite, a soma, etc.) may be determined using a nanoscale wire in electrical communication with the neuron; for instance, the neuron may depolarize (e.g., due to exposure to a chemical species, or to a nanoscale wire or other electrode able to cause the neuron to depolarize), causing the formation and propagation of an action potential through the neuron, which action potential may be determined using a microneedle as described herein. In this way, one or more than one neuron may be studied. In some embodiments, electrical signals from one or more neurons forming an interconnected network may be recorded using one or more microneedles.

In some embodiments, the electrical state of the cell may be altered by exposing the cell to a chemical species suspected of being able to alter the electrical state of the cell. For example, a chemical species able to facilitate the depolarization of a cell, or a chemical species that inhibit the depolarization of a cell, can be used to alter the electrical state of the cell, and in some cases, to cause a cell such as a neuron to polarize (e.g., hyperpolarize) or depolarize. In one set of embodiments, the chemical species comprises drugs or drug candidates, neurotoxins, neurotransmitters, or the like, which may be suspected of being able to treat or alter the behavior of the cells. In some cases, the drugs or drug candidates may target one or more types of ion channels. As a non-limiting example, the drugs or drug candidates may target neuronal nicotinic acetylcholine receptors (nAchRs).

Due to their small size, more than one microneedle may be positioned in electrical communication with the cell, or portion thereof, according to another set of embodiments. For example, at least 3, at least 4, at least 5, at least 10, at least 15, at least 20, at least 25, at least 30, at least 35, at least 40, at least 45, or at least 50 or more microneedles may be positioned in electrical communication with the cell, or with a portion thereof, e.g., axons and/or dendrites if the cell is neuron. In some embodiments, more than one microneedle may be inserted in the cell, or portion thereof. For example, at least 3, at least 4, at least 5, at least 10, at least 15, at least 20, at least 25, at least 30, at least 35, at least 40, at least 45, or at least 50 or more electrodes may be inserted in the cell, or with a portion thereof. In embodiments, up to about 100 electrodes are inserted into the cell. Up to about 50 microelectrodes can be inserted into the cell. In certain embodiments, up to about 25 electrodes are inserted into the cell. Thus, a plurality of microneedles may each be used in some embodiments to independently measure a distinct region of the cell. If more than one nanoscale wire is present, the microneedles may each independently be the same or different. Non-limiting examples of microneedles include any of those described herein.

In various exemplary methods, the microelectrode arrays disclosed herein can be employed in microengineered physiological systems to assist with electrophysiological stimulation and recording of electrically active cellular populations.

In various embodiments and through the use of the microelectrode arrays disclosed herein, the present disclosure provides for high-throughput electrophysiological stimulation and recording methods to assess biometric properties of microengineered neural tissue that mimics native anatomical and physiological features. Methods of using the presently disclosed microelectrode arrays provide novel approaches to evaluate neural physiology in vitro, using the compound action potential (CAP) as a clinically analogous metric to obtain results that are more sensitive and predictive of human physiology than those previously available.

One aspect of the present disclosure provides a method for measuring the functions of various cellular targets, including but not limited to, microtubules, ion channels, myelin, mitochondria, and the small nerve fibers. In certain embodiments, the invention includes a method for measuring the myelination of axons using the microelectrode array and the in vitro model described herein. Similar to the structure of a human afferent peripheral nerve, dorsal root ganglion (DRG) neurons in these in vitro constructs project long, parallel, fasciculated axons to the periphery. In native tissue, axons of varying diameter and degree of myelination conduct sensory information back to the central nervous system at different velocities. Schwann cells support the sensory relay by myelinating axons and providing insulation for swifter conduction. Similarly, the three-dimensional growth induced by this in vitro construct comprises axons of various diameters in dense, parallel orientation spanning distances up to 10 mm Schwann cell presence and sheathing can be observed in confocal and TEM imaging.

Although neuronal morphology is a useful indicator of phenotypic maturity, a more definitive sign of healthy neurons is their ability to conduct an action potential. Apoptosis alone is not a full measure of the neuronal health, as many pathological changes can occur before cell death manifests. Electrophysiological studies of action potential generation can determine whether the observed structures support predicted function, and the ability to measure clinically relevant endpoints produces more predictive results. Similarly, information gathered from imaging can determine quantitative metrics for the degree of myelination, while CAP measurement can demonstrate the overall health of myelin and lends further insight into toxic and neuroprotective mechanisms of various agents or compounds of interest.

As used herein, the "at least one agent" can refer to a small chemical compound. In some embodiments, the at least one agent comprises at least one environmental or industrial pollutant/compound. In certain embodiments, the at least one agent comprises one or a combination of small chemical compounds chosen from: chemotherapeutics, analgesics, cardiovascular modulators, cholesterol, neuroprotectants, neuromodulators, immunomodulators, anti-inflammatories, and anti-microbial drugs.

The at least one agent can comprise one or a combination of chemotherapeutics. Exemplary chemotherapeutics include any one or more of the following: Actinomycin, Alitretinoin, All-trans retinoic acid, Azacitidine, Azathioprine, Bexarotene, Bleomycin, Bortezomib, Capecitabine, Carboplatin, Chlorambucil, Cisplatin, Cyclophosphamide, Cytarabine, Dacarbazine (DTIC), Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Irinotecan, Mechlorethamine, Melphalan, Mercaptopurine, Methotrexate, Mitoxantrone, Nitrosoureas, Oxaliplatin, Paclitaxel, Pemetrexed, Romidepsin, Tafluposide, Temozolomide (Oral dacarbazine), Teniposide, Tioguanine (formerly Thioguanine), Topotecan, Tretinoin, Valrubicin, Vemurafenib, Vinblastine Vincristine, Vindesine, Vinorelbine, Vismodegib, and Vorinostat. In embodiments, the at least one agent comprises one or a combination of analgesics. Exemplary analgesics include, but are not limited to: Paracetoamol, Non-steroidal anti-inflammatory drugs (NSAIDs), COX-2 inhibitors, opioids, flupirtine, tricyclic antidepressants, carbamaxepine, gabapentin, and pregabalin.

In some embodiments, the at least one agent comprises one or a combination of cardiovascular modulators. Cardiovascular modulators can include, but are not limited to: nepicastat, cholesterol, niacin, scutellaria, prenylamine, dehydroepiandrosterone, monatepil, esketamine, niguldipine, asenapine, atomoxetine, flunarizine, milnacipran, mexiletine, amphetamine, sodium thiopental, flavonoid, bretylium, oxazepam, and honokiol.

In some embodiments, the at least one agent comprises one or a combination of neuroprotectants and/or neuromodulators. Exemplary neuroprotectants and/or neuromodulators include: tryptamine, galanin receptor 2, phenylalanine, phenethylamine, N-methylphenethylamine, adenosine, kyptorphin, substance P, 3-methoxytyramine, catecholamine, dopamine, GABA, calcium, acetylcholine, epinephrine, norepinephrine, and serotonin.

The at least one agent can comprise one or a combination of immunomodulators. Exemplary immunomodulators include: clenolizimab, enoticumab, ligelizumab, simtuzumab, vatelizumab, parsatuzumab, Imgatuzumab, tregalizaumb, pateclizumab, namulumab, perakizumab, faralimomab, patritumab, atinumab, ublituximab, futuximab, and duligotumab. In some embodiments, the at least one agent comprises one or a combination of anti-inflammatories. Exemplary anti-inflammatories include: ibuprofen, aspirin, ketoprofen, sulindac, naproxen, etodolac, fenoprofen, diclofenac, flurbiprofen, ketorolac, piroxicam, indomethacin, mefenamic acid, meloxicam, nabumetone, oxaprozin, ketoprofen, famotidine, meclofenamate, tolmetin, and salsalate.

In certain embodiments, the at least one agent comprises one or a combination of anti-microbials. The antimicrobials can include, but are not limited to: antibacterials, antifungals, antivirals, antiparasitics, heat, radiation, and ozone.

The at least one agent can comprise biological agents or "biologics." Biologics can refer to any agent or therapeutic that is produced from a living organism or contains a component that is found within living organisms. In embodiments, the "at least one agent" comprises immunoconjugates, small molecule drug conjugates, anti-sense oligonucleotides, nucleic acid therapies, viral vectors, small interfering RNA or a combinations thereof.

In some embodiments, an immunoconjugate can refer to an antibody conjugated to at least one effector molecule or at least one chemical compound. In embodiments, such conjugation can function to increase the efficacy of the antibody molecule for use as a diagnostic or therapeutic agent. Coupling of the antibody with the chemical compound can be accomplished by any mechanism or chemical reaction that binds the two molecules together without affecting the respective activities of the antibody or the chemical compound conjugated thereto. Suitable linking mechanisms include, but are not limited to, covalent binding, affinity binding, intercalation, coordinate binding, complexation, or a combination thereof. In certain embodiments, effector molecules comprise molecules having a desired activity, e.g., cytotoxic activity. Non-limiting examples of effector molecules which can be attached to antibodies include toxins, anti-tumor agents, therapeutic enzymes, radionuclides, antiviral agents, chelating agents, cytokines, growth factors, and oligo- or polynucleotides. Vectors can include chemical conjugates such as those described in WO 93/64701 (incorporated herein by reference), which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618; incorporated herein by reference) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Vectors can include viral vectors, fusion proteins and chemical conjugates. Retroviral vectors include moloney murine leukemia viruses. Vectors can include pox vectors such as orthopox or avipox vectors, herpesvirus vectors such as a herpes simplex I virus (HSV) vector, adenovirus vectors, and adeno-associated virus vectors.

Pox viral vectors can introduce the gene into the cells cytoplasm. Avipox virus vectors can result in only a short term expression of the nucleic acid. Adenovirus vectors, adeno-associated virus vectors, and herpes simplex virus (HSV) vectors are can introduce the nucleic acid into neural cells. The adenovirus vector can result in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, CaP04 precipitation, DEAE dextran, electroporation, protoplast fusion, lipofection, cell microinjection, and viral vectors. Vectors can be employed to target essentially any desired target cell.

Another aspect of the present disclosure includes a method of measuring both intracellular and extracellular recordings of biomimetic neural tissue in a three-dimensional culture platform. Previously, electrophysiological experiments were undertaken in either dissociated surface-plated cultures or organotypic slice preparations, with limitations inherent to each method. Investigation in dissociated cell cultures is typically limited to single-cell recordings due to a lack of organized, multi-cellular neuritic architecture, as would be found in organotypic preparations, such as the microengineered physiological systems disclosed herein. Organotypic preparations have intact neural circuitry and allow both intra- and extracellular studies. However, acute brain slices present a complex, simultaneous array of variables without the means to control individual factors and thus are inherently limited in throughput possibility.

The present disclosure provides a biomimetic three-dimensional neural culture that allows examination of population-level electrophysiological behavior. The systems and methods disclosed herein support whole-cell patch clamp techniques and synchronous population-level events in extracellular field recordings resulting from the confined neurite growth in a three-dimensional geometry.

Using the methods and devices disclosed herein, field recordings can be used to measure the combined extracellular change in potential caused by signal conduction in all recruited fibers. The population response elicited by electrical stimulation is a CAP. Electrically evoked population spikes are graded in nature, comprising the combined effect of action potentials in slow and fast fibers. Spikes are single, cohesive events with swift onsets and short durations that are characteristic of CAPs or responses comprised purely of action potentials with quick signal conduction in the absence of synaptic input. The three-dimensional neural constructs disclosed by the present disclosure also support CAPs stimulated from farther distances along the neurite tract or channel, demonstrating the neural culture's ability to swiftly carry signals from distant stimuli much like an afferent peripheral nerve. The three-dimensional neural cultures of the present disclosure support proximal and distal stimulation techniques useful for measuring conduction properties. In various embodiments, the microelectrode arrays disclosed herein are used for stimulation of a microengineered physiological system, recordation of CAPs, or both.

The systems and methods disclosed herein can be used with one or more growth factors that induce recruitment of numerous fiber types, as is typical in nerve fiber tracts. In particular, nerve growth factor (NGF) preferentially recruits small diameter fibers, often associated with pain signaling, as demonstrated in the data presented herein. It has been shown that brain derived neurotrophic factor (BDNF) and neurotrophic factor 3 (NT-3) preferentially support the outgrowth of larger-diameter, proprioceptive fibers. Growth-influencing factors like bioactive molecules and pharmacological agents can be incorporated with electrophysiological investigation to allow for a systematic manipulation of conditions for mechanistic studies. Additional suitable factors include, but are not limited to Forskolin, TGFB-1, GDNF, Glutamax, N2, B27, FBS, Rock inhibitor, ascorbic acid, BSA, and cAMP. In various exemplary methods, the presently disclosed microelectrode arrays can be used with microengineered physiological systems to study the mechanisms underlying various neurological disorders. By way of example, disclosed herein are methods of studying myelin-compromising diseases and peripheral neuropathies by investigating the effects of known dysmyelination agents, neuropathy-inducing culture conditions, and toxic neuropathy-inducing compounds on the neural cultures. The present disclosure permits conduction velocity to be used as a functional measure of myelin and nerve fiber integrity under toxic and therapeutic conditions, facilitating studies on drug safety and efficacy. The incorporation of genetic mutations and drugs into neural cultures produced using the techniques disclosed herein can enable the reproduction of disease phenomena in a controlled manner, leading to a better understanding of neural degeneration and possible treatment therapies.

The microelectrode arrays can be used to study pathophysiological mechanisms of toxicity, disease, or any agent within any cell population or to study the effects of toxicity, disease, or any agent on any aspect or component of a cell. By way of example, the various embodiments disclosed herein can be applied to study any contents of a cell, cell membranes, or components of cell membranes. Embodiments can be applied to cell organelles, subcellular organelles, cell cytoplasm, structures within the cell membrane, or a combination thereof. Certain embodiments can be applied to study, microtubules, chromosomes, DNA, RNA, mitochondria, ribosomes, Golgi apparatus, lysosomes, endoplasmic reticulum, vacuoles, fragments of any of the foregoing, or other contents or fragmental contents of a cell. Structures within the cell membrane can include any membrane proteins, membrane channels, membrane receptors, or a combination thereof. Embodiments can be applied to studying cellular interactions with the environment.

Another aspect of the present invention includes a medium to high-throughput assay of neurological function for the screening of pharmacological and/or toxicological properties of chemical and biological agents. In embodiments, the agents are cells, such as any type of cell disclosed herein, or antibodies, such as antibodies that are used to treat clinical disease. In embodiments, the agents are any drugs or agents that are used to treat human disease such that toxicities, effects, or neuromodulation can be compared among a new agent which is a proposed mammalian treatment and existing treatments from human disease. In some embodiments, new agents for treatment of human disease are treatments for neurodegenerative disease and are compared to existing treatments for neurodegenerative disease. In the case of multiple sclerosis as a non-limiting example, the effects of a new agent (modified cell, antibody, or small chemical compound) can be compared and contrasted to the same effects of an existing treatment for multiple sclerosis such as Copaxone, Rebif, other interferon therapies, Tysabri, dimethyl fumarate, fingolimod, teriflunomide, mitoxantrone, prednisone, tizanidine, baclofen, or a combination thereof.

In one aspect, the present invention provides methods of replicating, manipulating, modifying, and evaluating mechanisms underlying myelin-compromising diseases and peripheral neuropathies.

In another aspect, the present disclosure includes medium to high-throughput assays of neuromodulation in human neural cells for the screening of pharmacological and/or toxicological activities of chemical and biological agents.

In various aspects, the presently disclosed microelectrode arrays are employed in conjunction with unique microengineered physiological systems, such as 2D and 3D microengineered neural bundles, in combination with optical and electrochemical stimulation to permit recording of human neural cell populations.

Also provided herein are methods of quantifying evoked post-synaptic potentials in a biomimetic, microengineered physiological systems that specifically mimic peripheral neural circuitry, central neural circuitry, or a combination thereof. In embodiments, the microelectrode array is used to study population-level physiology, such as the conduction of compound action potentials and postsynaptic potentials. In certain embodiments any of the various microelectrode arrays disclosed herein can be used to study interactions between separate microengineered physiological systems. By way of example, the microelectrode array can detect interactions between at least two independent organoid systems, between at least two independent organ-on-a-chip systems, between at least one organoid system and at least one organ-on-a-chip system, or a combination thereof.

In another aspect, optogenetic methods, hardware and software control of illumination and fluorescent imaging are used in association with the microelectrode arrays disclosed herein to permit noninvasive stimulation and recording of multi-unit physiological responses to evoked potentials in neural circuits.

Additional methods include the study employing the microelectrode arrays in testing selective 5-HT reuptake inhibitors (SSRIs) and second-generation antipsychotic drugs to see if they alter their developmental maturation.

In various aspects, the methods of can further comprise histological or morphological analysis of the neural tissue. In embodiments, histological analysis comprises an assessment of axon diameter, axon density, myelination, cell morphology, cell type, nerve structure, or a combination thereof. In certain embodiments, electrophysiological testing can comprises stimulating a plurality of locations along the axonal growth region, the ganglion region, or a combination thereof and recording a resultant electrical response from the ganglion region, the axonal growth region, or a combination thereof. In embodiments, data obtained from histological analysis is correlated with data obtained from electrophysiological testing. Certain inferences of neural pathology can be drawn based on the correlation between the histological data and the electrophysiological data. Certain embodiments further comprise comparing nerve conduction velocity obtained from sample neural tissue to that of neural tissue that is known to be healthy neural tissue, wherein reduced nerve conduction in the sample neural tissue as compared to the healthy neural tissue indicates a neural pathology. In embodiments, relative changes in morphology, phenotype, genotype, structure, electrophysiology, or a combination thereof can be compared between sample neural tissue to that of healthy neural tissue or between sample neural tissue and neural tissue that has been subjected to at least one agent. In certain embodiments, the electrophysiological testing, histological/morphological testing, or a combination thereof are performed over a multi-week period to chronically measure neurodegeneration or to track neuronal cells during maturation or development.

The disclosure of PCT/US2019/049802 is incorporated herein in its entirety as background and support information.

In another various exemplary embodiments, the microelectrode arrays disclosed herein are used to infer conduction velocity as a functional measure of neural tissue condition under toxic and therapeutic conditions. Information on degree of myelination, myelin health, axonal transport, mRNA transcription, neuronal damage, or a combination thereof can be determined from electrophysiological analysis. Taken in combination with morphometric analysis such as nerve density, myelination percentage, and nerve fiber type, mechanisms of action can be determined for compounds of interest. In some embodiments, the devices, methods, and systems disclosed herein can incorporate genetic mutations and drugs to reproduce disease phenomena in a controlled manner, leading to a better understanding of neurological disorders and possible treatment therapies.

Example 1: A Makerspace Based Stainless Steel 3D
Microelectrode Array (MEA) on Glass Substrate
for Optical and Electrical Probing of Electrogenic
Cells I. Introduction Cells have a membrane potential that is the basis for integrating, generating, driving and transmitting signals from cells to the external environment.[1] Changes in ionic permeability translate into the electrical activity that regulates cellular physiology. Phenomena such as the potential from cardiac action, neurotransmission and production of neurotransmitters, cell proliferation, activation and differentiation, ion transport and the release of hormones are based on electrical activity.[2] Cellular electrophysiology is the study of the electrical properties of biological cells and tissues, which is necessary to understand and interpret their electrical activity.[3, 4] MicroElectrode Arrays (MEAs) are one of the interfaces used to record and stimulate electrical activity from the in vitro electrogenic cell cultures and serve as label-free platform in the pharmaceutical industry to provide information for instance about a drug's efficacy. MEAs have become vital in different fields such as pharmacology, toxicology, high throughput screening, stem cell differentiation etc. to obtain in vitro results of electrical measurements of different neurons, cells, tissues, etc.[5] MEAs are increasingly being used for disease-on-a-chip models for neural diseases such as Parkinson's, epilepsy, Amyotrophic Lateral Sclerosis (ALS), neuropathic pain, and autism spectrum disorders.[6] MEAs can therefore perform clinically relevant nerve conduction tests and measure changes in electrophysiological properties that reflect the effects on the human nervous system. MEA culturing chips are also used for cardiac cell therapeutics or to improve the existing cardiac safety mechanisms. MEAs serve as a platform to evaluate arrhythmia risk as such studies are vital to understanding the complex and varied nature of arrhythmia.[7] MEA technology plays an important role in advancing human health by pushing the boundaries of disease modeling and therapeutics including drug discovery along with safety and toxicology studies. It may be noted here that conventional MEAs are planar (2D) in nature and can be fabricated in "state of the art" cleanroom facilities.

To better mimic in vivo like conditions[8, 9] for in vitro applications, 3D cell culture models are becoming increasingly appropriate as they are capable to better capture signaling pathways and drug responsiveness in disease states when compared to 2D models. 3D cell cultures enable the formation of dynamic, spatial gradients of soluble factors that influence cellular migration, cell to cell communication and differentiation to accurately predict in vivo tissue functions and drug activities. This has led to an increasing need to extend cell culture matrices and support scaffolds to the third dimension.[9] Such cultures would help realize "disease on a plate" and fully functional "organ on a chip" models to promote cell/tissue growth and regeneration in vitro.[10] This has resulted in a growing need to extend in vitro MEAs to the third dimension. 3D MEAs would allow for simple, high throughput screening and measurement of network dynamics for the study of 3D microengineered cellular systems including but not limited to central or peripheral nervous system applications like the recently developed Human Nerve-on-a-Chip (HNoaC) system which is 3D in nature and can be used for evaluating electrophysiological and histological metrics[11] and other organ systems like having extracellular microelectrode recordings from cardiac myocytes in vitro Heart-on-a-Chip models.[12] Enabling 3D functionality in MEAs built atop optically transparent materials would enable simultaneous extraction of optical and electrical data from 3D cell cultures. Microfabrication of 3D MEAs using conventional cleanroom-based techniques is challenging because most of the techniques are suited for two-dimensional device processing. Additionally, backend technologies (such as Printed Circuit Boards or PCBs) are required to interface the fabricated device with commercial amplification systems for data processing, analysis and plotting.[6]

This Example 1 pertains to the microfabrication and packaging of a stainless steel (SS) 3D MEA assembled on a glass platform. The device fabrication employs non-traditional "Makerspace Microfabrication"[13-15] techniques to realize the device predominantly outside of the clean room. Laser micromachining is used to ablate a SS sheet with ten (10) obelisk like geometries. Eight (8) obelisk are arranged in a linear array and is terminated by two (2) obelisk adjacent to one another. The dimensions of the obelisk ablation is designed to have a height of 400 μm and a width of 300 μm once it is transitioned out-of-plane to have a 3D configuration. The pitch of the "obelisk is 600 μm in the linear portion of the array. Such a configuration may specifically be useful for some 3D cell cultures like the Human Nerve-on-a-Chip (HNoaC) system.[11] However, the 3D configuration is versatile and may be used for any 3D cell culture, tissue slices and cell clusters. The tip of the obelisk geometry can also penetrate the tissue and make recording from inner cell layers as the outer cell layer often contains dead cells which shield the cell signals of inner cell layers from the electrodes. The 3D obelisk array is subsequently assembled on a highly transparent glass chip with metallized titanium-gold (Ti—Au) traces making the platform capable of simultaneous optical and electrical probing. The array of electrodes is isolated from each other by laser micromachining to have ten (10) individual recording/stimulation sites. Polydimethylsiloxane (PDMS) having a thickness of ~250 μm is used as an insulation material and is defined by controlled precision drop-casting technique (CPDC). The CPDC can be optimized to realize 3D electrodes of varying sizes as the PDMS casting is performed after affixing the Polyethylene Terephthalate Glycol (PET-G) culture well onto the glass chip which restricts the insulation material (PDMS) within the confines of the culture well. The microfabricated 3D MEAs having an area of ~0.03 mm² demonstrates an impedance and phase of ~6.9 kΩ and −12.3° at an electrophysiological relevant frequency of 1 kHz. To interface the fabricated device with commercially available data acquisition systems a custom designed 3D printed interconnect frame with vias and channels is fabricated. The vias and channels are filled with conductive paste by silver ink casting which allows for the transition of the probing pads on the top side of the glass chip to the bottom side of the packaged device with the 3D printed ink-casted frame. It will be appreciated by those skilled in the art that the silver ink can be substituted with other suitable materials, such as, but not limited to, gold, graphene, carbon nanotubes and the like. The performance of the 3D MEA with the 3D printed frame demonstrates an impedance and phase of ~13.3 kΩ and −12.1° at the electrophysiological relevant frequency of 1 kHz. Extracted values of the circuit elements corresponding to the Randles' equivalent of the 3D MEA before and after integrating with the frame indicate that the values are within acceptable tolerance limits. HL-1 cells, a cardiac muscle cell line from the AT-1 mouse that contracts and retains phenotypic characteristics of the adult cardiomyocyte were cultured on the devices to assess their biocompatibility and signal quality with the fully finished devices. Cellular electrophysiological activity was measured after approximately 2 days in vitro (DIV). A classic action potential was captured from the 3D MEA platform demonstrating the capability of the device as a cost effective, rapidly fabricated biosensing platform for medical and pharmaceutical research.

II. Materials and Methods (a) Microfabrication of 3-Dimensional Stainless Steel Microneedle Electrodes The obelisk like microneedle array was designed using SolidWorks, Dassault Systems Inc., MA, USA in Drawing Interchange format (.dxf). The length of the construct was 4200 μm with a width 500 μm terminating with a circular region having a diameter of 800 μm. Ten (10) microneedles were placed inside the described silhouette and the microneedle cutout had a base width of 300 μm, length of 400 μm and a pitch of 600 μm. FIG. 1 (a) shows the schematic of the laser micromachining of the SS sheet (25 μm thick) 20 micromachined with infrared laser wavelength (1064 nm) using the QuikLaze 50 ST2 laser micromachining system (Eolite Lasers, OR, USA). The laser was operated at a repetition rate of 50 Hz with a scanning speed of 40 μm/s. The obelisk cut-outs 22 in SS 20 were transitioned out of plane into a 3D configuration using a hypodermic needle 23 [FIG. 1 (b)]. Although a hypodermic needle is shown in this embodiment, any structure capable of transitioning the cut-outs 22 out of plane are can be utilized as a transition structure. FIG. 1 (c) shows the schematic of the 3D microneedles 25 after it has been released from the SS substrate 20 and the inset shows the cutout 26 in the SS substrate 20 which would be used in subsequent processing steps as a shadow mask.

(b) Assembly and Packaging of the Device

Figures 2A, 2B, 2C, 2D, 2E, 2F, 2G, 2H, 2I:
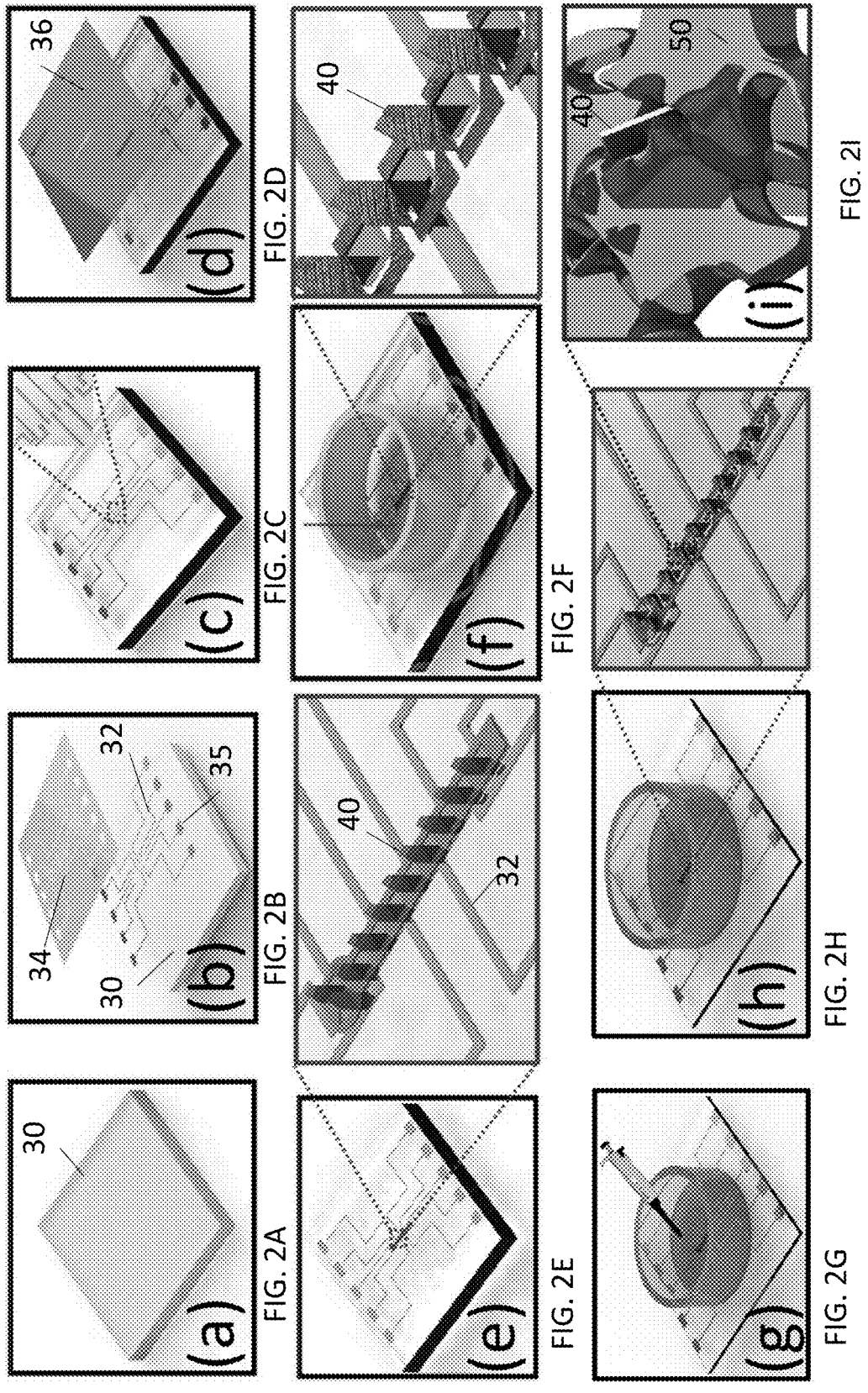
FIG. 2A-2I show a Schematic Process Flow of glass chip fabrication and stainless steel assembly.

The SS 3D electrodes were assembled on a highly transparent glass chip 30 (22 mm×22 mm×0.5 mm) to allow for simultaneous optical and electrical probing [FIG. 2 (a)]. The glass substrate 30 was first cleaned in KOH (potassium hydroxide) in IPA (isopropyl alcohol; 2-propanol). It is noted that the glass substrate can be substituted with a different transparent substrate including but not limited to transparent polymer, such as Polystyrene, Polycarbonate, Cyclic Olefin Copolymer, PolyEthylene Terephthalate, and the like. For electrical probing from the 3D microneedle array, traces 32 of (Ti; 4N5 purity pellets) and gold (Au; 5N purity pellets) (Kurt J. Lesker, PA, USA) were deposited by electron-beam (E-beam) evaporation (Thermionics Laboratory Inc., USA) through a shadow mask 34 fabricated out of Kapton. The shadow mask design had probing pads 35 in place for vias of the 3D printed frame, which was retrofitted to the glass chip 30 [FIG. 2 (c)]. The traces 32 and probing pads 35 for the shadow mask 34 were designed in SolidWorks. The traces are designed to be 150 μm wide and ~7-16 mm long depending upon the position of the electrode and the pad. The dimension of the pads was 1×1 mm with a pitch of 4 mm. The Kapton mask 34 was ablated with a QuikLaze 50 ST2 laser micromachining system (Eolite Lasers, USA) (UV wavelength: 355 nm, scanning speed of 70 μm/s, repetition rate: 50 Hz) [FIG. 2 (b)]. Subsequently, the SS key-shaped cutout mask 36 [FIG. 2 (d)] was placed on top of the glass chip 30 and aligned with the central region of the glass chip [FIG. 2 (c)] and the 3D microneedles 40 were bonded to the glass substrate with silver paste; PRIMA-SOLDER™ EG8050, AI Technology, NJ, USA [FIG. 2 (d)]. Curing of the silver paste was performed for a period of 48 hours at 55° C. in an oven. [FIG. 2 (e)] shows the schematic of the device after the 3D microneedles 40 were bonded onto the glass chip 30 with traces 32. PET-G (Polyethylene Terephthalate Glycol) culture wells 42 having an outer diameter of 16 mm and an inner diameter of 14 mm were bonded with PDMS (Poly Dimethyl Siloxane, Chemical Formula: $(C_{10}H_8O_4)_n$) to act as a biocompatible adhesive layer [FIG. 2 (f)]. The PET-G culture rings 42 were cut from a parent tube using a Horizontal Band Saw, Wellsaw, MI, USA. Both the PET-G culture well and PDMS are biocompatible which makes the MEA chip suitable for biological applications.[9, 16]

3D microneedle electrodes 40 were isolated from each other using QuikLaze 50 ST2 laser micromachining (IR wavelength: 1064 nm, scanning speed of 40 μm/s, repetition rate: 50 Hz) so that the device has (N=10) recording/stimulating sites [FIG. 2 (f)]. The laser micromachining process was able to ablate all the way through the SS substrate and the underlying silver paste but stop on glass due to the precision ablation capabilities and multimodality of the system which allows for switching between several wavelengths to ablate specific materials. Insulation of the traces 32 and electrodes (microneedles) 40 to realize the 3D MEA was performed with a PDMS drop-casting step inside the PET-G culture well. This Controlled Precision Drop Casting (CPDC) technique [FIG. 2 (g)] allows for controlling the size/area of the 3D MEA. The PDMS was cured for 18 hours at 50° C. to realize the final device [FIG. 2 (h)]. FIG. 2 (i) shows a schematic of HL-1 cells 50 interacting with a singular microneedle 40.

Figure 3B:
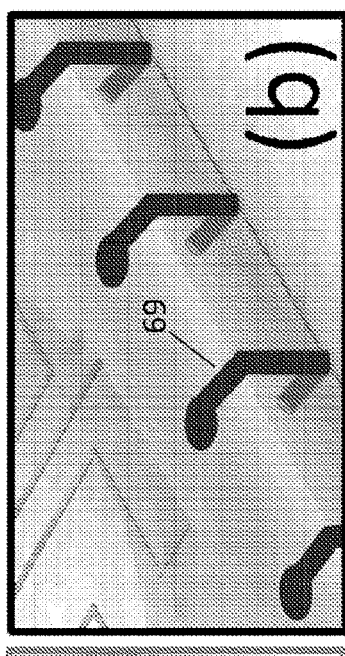
FIGS. 3A-3B show a Schematic Process Flow of interconnect fabrication.
Figure 3B:
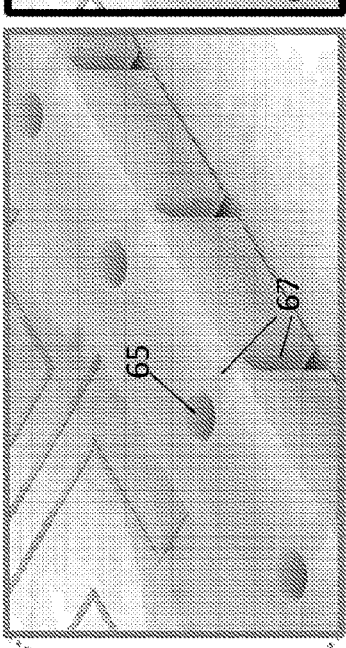
Figure 3A:
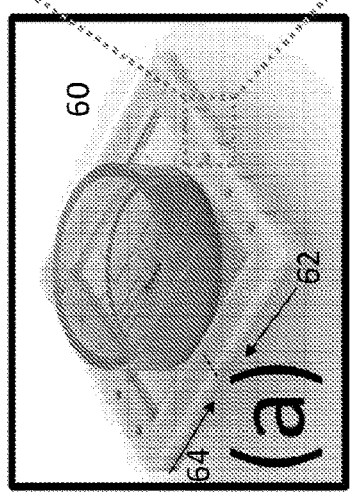

(c) Integration of Custom 3D Printed, Interconnect Packaging Frame for Interfacing with Commercial Electronics Amplification Systems CAD design using SolidWorks 3D was used to design a custom interconnect packaging frame for interfacing with commercial electronics amplification systems such as Axion BioSystems MUSE.[17] The packaging frame 60 comprises two parts 62, 64 which slide onto the glass chip on either side as seen in FIG. 3 (a). The length of the frame 60 is 24 mm with a width 12 mm and a thickness of 2 mm, all dimensions to be consistent with the modified MUSE system. The frames are designed to have ~510 μm grooves (not shown) onto which the glass chip of thickness ~500 μm slides inside. Each frame 62, 64 has a total of five vias 65, whose dimensions were 1 mm in diameter and coincide over the positions of the contact pads (hidden) on the glass chip. The vias 65 transition the contact pads electrically from the top side of the glass chip to the bottom side 3D printed frame once the vias 65 and the channels 67 are filled completely with conductive silver paste [FIG. 3 (b)]. The frames 62, 64 were 3D printed on the Asiga MAXUV Digital Light Processing (DLP) System, Australia with high temperature resin (RS-F2-HTAM-02, Formlabs, MA, USA). After the material was printed, it was washed for 10 minutes with Isopropyl alcohol (IPA) and dried in an oven. The 3D printed frame 60 was finally cured in an UV enclosure (385 nm UV wavelength) of a period of 180 seconds to completely crosslink the resin and cure the interconnect frames. The purpose of the vias 65 and channels 67 is to provide the interconnection between the top to bottom sides using an ink casting step with silver adhesive 69 [FIG. 3 (b)]. Impedance measurements of the 3D MEA were performed using Bode 100 (Omicron Labs, Houston, TX, USA) with Dulbecco's Phosphate Buffer Solution (Thermo Fisher Scientific, Waltham, MA, USA) as the electrolyte. The impedance scans were carried out from 100 Hz to 1 MHz with a platinum wire (eDAQ, Denistone East, Australia) as the counter electrode.

(d) Cardiac Cell Culture

In order to determine the ability of the microfabricated and assembled device to capture electrophysiological activity, HL-1 cells (an electrogenic cell line) were grown on the device. HL-1 cells are immortalized mouse atrial cardiomyocytes that continuously divide and spontaneously contract in culture.[18] Cells were cultured for 48 hours in cell culture flask (T25 Fisher Scientific) with sterile Claycomb medium (Sigma-Aldrich; 51800C-500ML). HL-1 cells were passaged when they reached confluency. MEAs were sterilized with IPA (Isopropyl alcohol) and pre-coated with gelatin/fibronectin extracellular matrix coating for 12 hours prior to plating the HL-1 cells (approximately 31,000 cells). Claycomb cellular medium was changed every day. Electrophysiological measurements were performed by interfacing the device with the Axion MUSE after 2 DIV (days in vitro) on the 3D glass MEA. Spiking activity 6 times above the root mean square (RMS) noise of the system where recorded as action potentials.

Figures 4A, 4B, 4C, 4D, 4E, 4F:
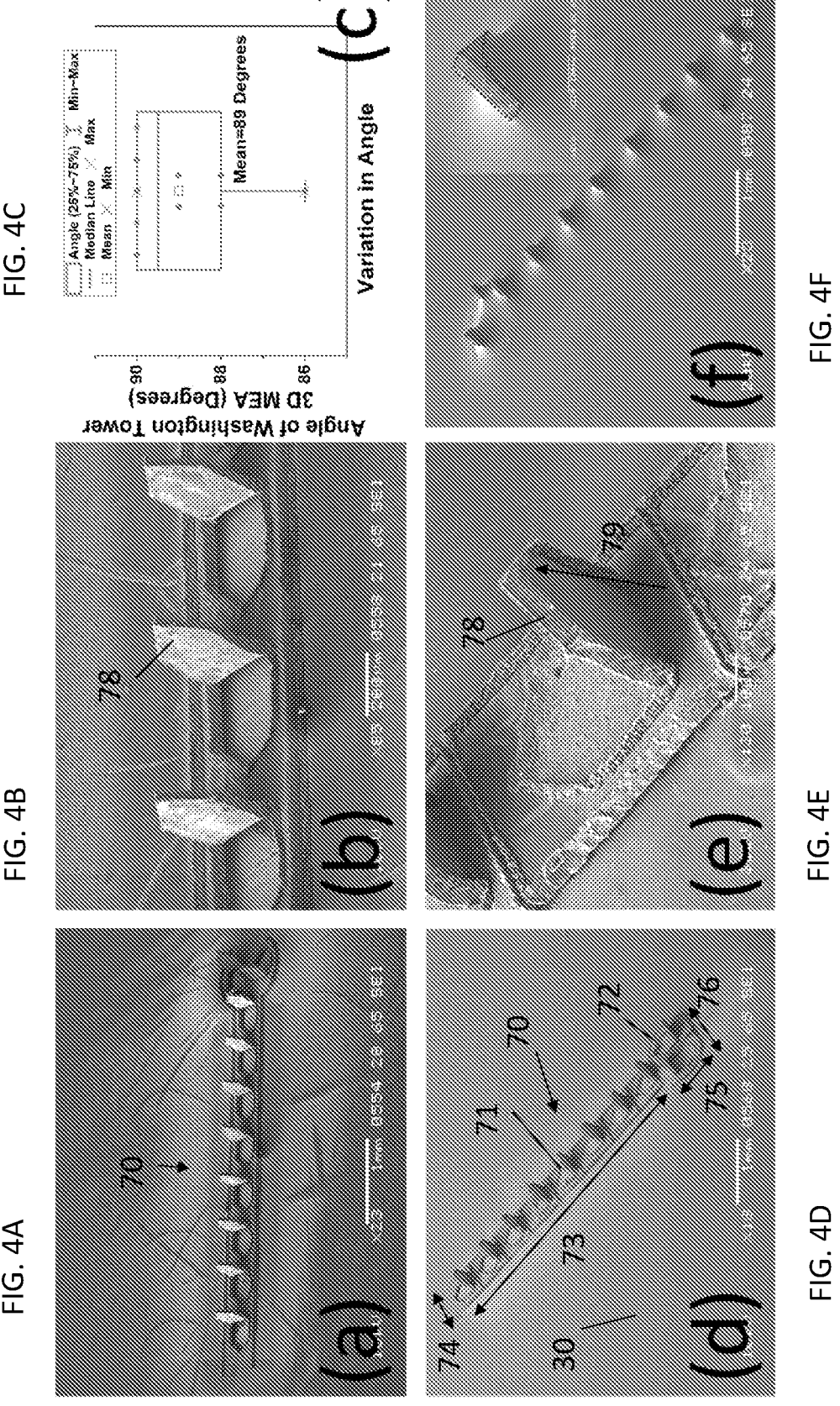
FIGS. 4A-4F show SEM images of the Washington Tower 3D microneedles after each of the microneedles have been transitioned out-of-plane. The key-shaped pattern has not been released from the stainless steel substrate as seen in (FIG. 4A). The close-up SEM images of the 3D microneedles is shown in (FIG. 4B).

III. Results and Discussions (a) Microfabrication of 3-Dimensional Stainless Steel Microneedle Electrodes FIG. 4 (a) shows the SEM images of the 3D microneedle array 70 after it has been transitioned out-of-plane using a hypodermic needle. FIG. 4 (b) shows a close up SEM image of the 3D microneedle electrodes 78. Microneedles were perpendicular with respect to the horizontal. A box plot of the angular tilt of the 3D microneedles is further shown in FIG. 4(c) emphasizing the consistency of angles of every 3D microneedle with respect to the horizontal. For a total of 10 electrodes, the maximum angle of tilt was 90° with a minimum of 86°. An average value of 89° with respect to the horizontal was obtained for the 3D microelectrodes. FIG. 4 (d) depicts an SEM image of the 3D microneedles 70 bonded to the glass substrate 30 using silver paste after laser isolation of the ten (10) recording/stimulating sites. As shown, in FIG. 4(d), the 3D microneedles 70 include a first portion 71 and a second portion 72 microneedles 78. The first portion 71 includes a length dimension 73 and a width dimension 74. The second portion includes a length dimension 75 and a width dimension 76. As shown, the first length dimension 73 is larger than the second length dimension 75 and the second width dimension 76 is larger the first width dimension 74. The first portion 71 and second portion 72 form a geometry such that the first portion that aligns with a neural tract of a nerve cell and the second portion 72 aligns with a ganglion of the nerve cell when placed on the plurality of microneedles 70. FIG. 4 (e) shows a close up SEM image depicting the scribe lines of the laser to isolate the microneedle electrode array. A single microneedle 78 has a height dimension 79 according to the height options described above. FIG. 4 (f) depicts an SEM image of the completed 3D MEA after CPDC process using PDMS insulation. It is seen that the CPDC technique insulates the entire device and exposes the SS tips at a height of ~400 μm to realize the 3D MEA as seen in the inset of FIG. 4 (f). 3D microneedles SEM images in figure [FIG. 4 (b, c, d)] remained remarkably close to the design dimensions of 400 μm height, 300 μm width (N=10 in an array) at a pitch of 600 μm.

Figures 5A, 5B, 5C, 5D, 5E, 5F:
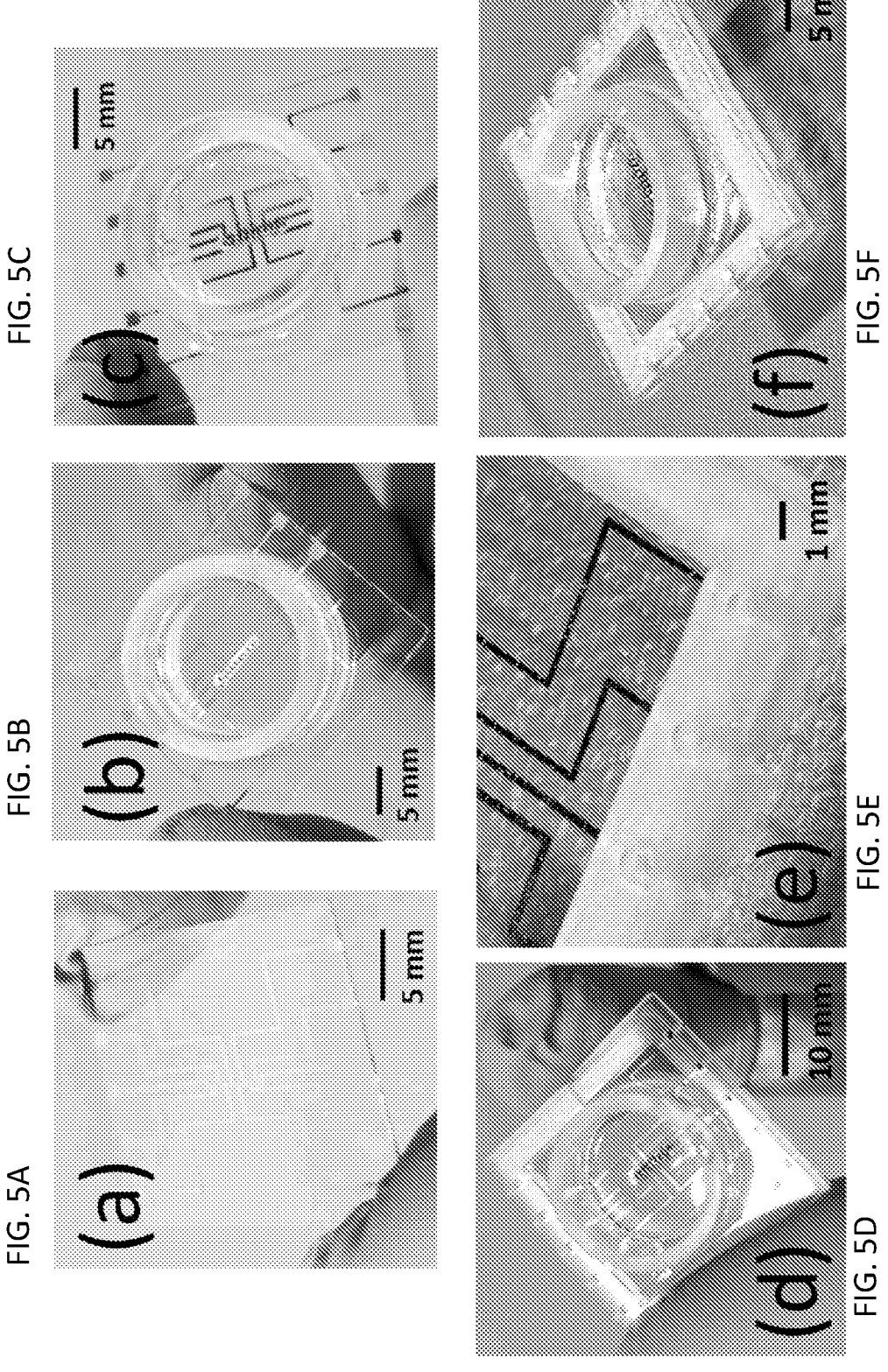
FIGS. 5A-5F show optical microphotographs of the fully assembled device.

FIG. 5 show the microphotographs of the device fabrication and assembly in various stages of realizing the 3D MEA. FIG. 5 (a) shows the microphotograph of the Ti—Au traces as obtained after e-beam evaporation through the laser-cut Kapton shadow mask. FIG. 5 (b) shows the microphotograph of the device after the 3D microneedles are bonded to the glass substrate using silver paste. The 3D microneedles are subsequently laser micromachined to be isolated from each other and insulation of the traces and microneedles is achieved via PDMS CPDC inside the PET-G culture well to yield the assembled device [FIG. 5 (c)]. FIG. 5 (d) shows the microphotograph of the device with the 3D printed frames slid on each sides of the glass chip to have the final packaged device. FIG. 5 (e) shows a close-up image of the 3D printed frame with the vias which can be subsequently filled with silver paste to transition the gold pads on the glass chip to the bottom side of the 3D printed frame with the help of the ink-cast microchannel on the outer rim of the 3D printed part [FIG. 5 (f)].

(b) Electrical Characterization

Figures 6A, 6B, 6C, 6D:
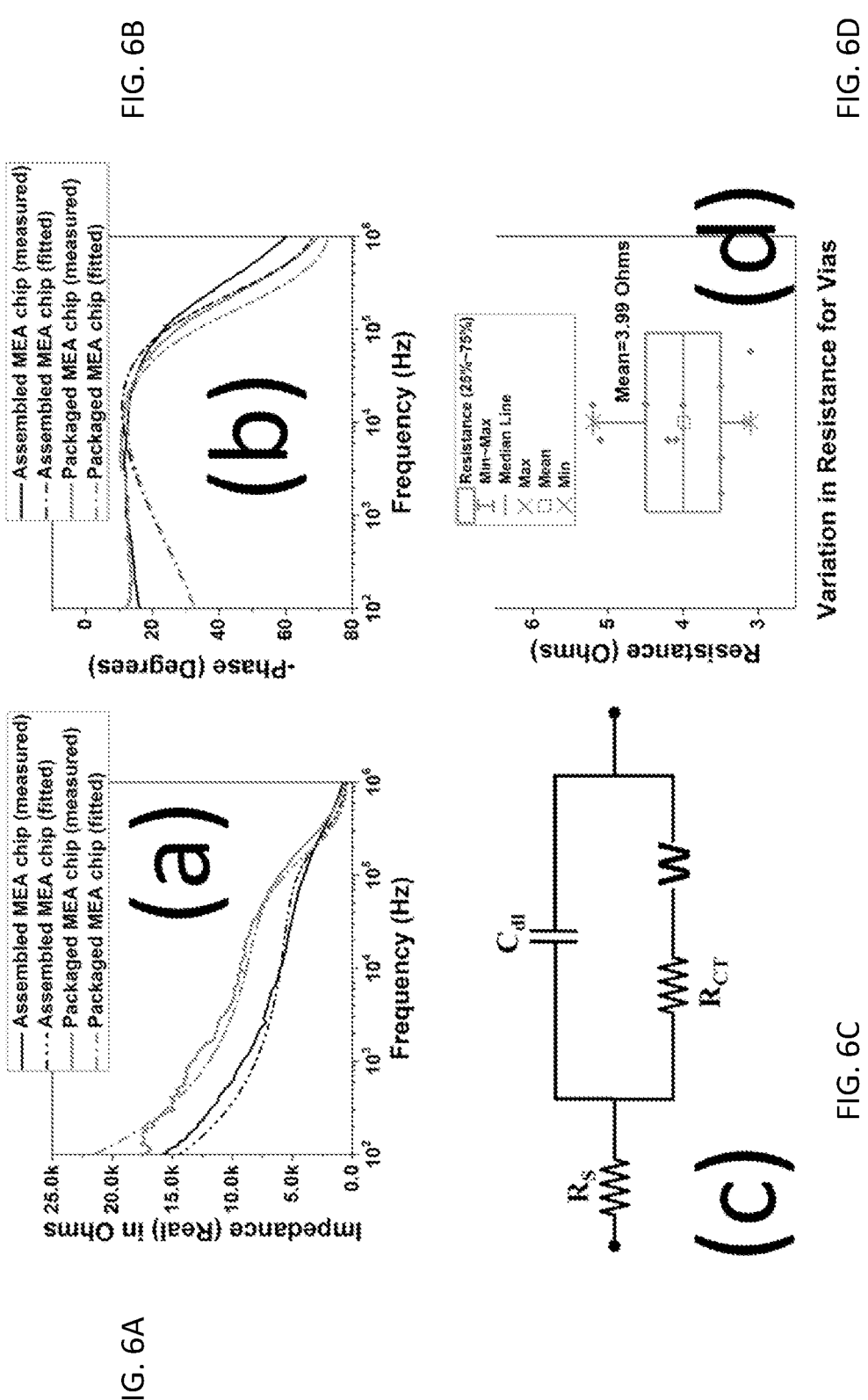
FIGS. 6A-6D.

Full spectrum impedance measurements of the 3D MEAs were measured in conductive saline media. FIGS. 6 (a) and (b) show the impedance spectra of the 3D MEAs after they were assembled and packaged for N=3 electrodes. The measured values were fitted with Randles' circuit model [FIG. 6 (c)], a common impedance model used for microelectrodes.[19, 20] Both these data sets are very similar depicting minimal change from 3D microneedle assembly on glass to attachment with the 3D primed frame. The average impedance (real) was 6.9 kΩ with phase of −12.30@ 1 kHz for the assembled device. With the packaged device the average impedance (real) was 13.3 kΩ with phase of −12.1°@1 kHz. These values were similar to other reports in literature for similar sized electrodes.[9, 21, 22]

Further, from the extracted parameters [Table 1] it is seen that the 3D printed frame does not affect the performance of the 3D MEA, especially for the values of the double layer capacitance ($C_{DL}$) and $R_s$ which remain unaltered. Changes in Charge Transfer Resistance ($R_{CT}$) and the Warburg element were additionally observed to be within expected limits.[21, 23-25]. This was attributed to the very low DC resistance of the silver ink casted vias in the 3D printed frame. FIG. 6 (d) shows the box plot of the DC resistance of N=10 vias. The mean resistance of this set of vias was 3.99Ω. The differences in results were less than ±1.00Ω when compared to the mean.

(c) Axion Biosystem MEAs Noise Measurement with HL-1 Cell

Figures 7A, 7B, 7C, 7D, 7E, 7F:
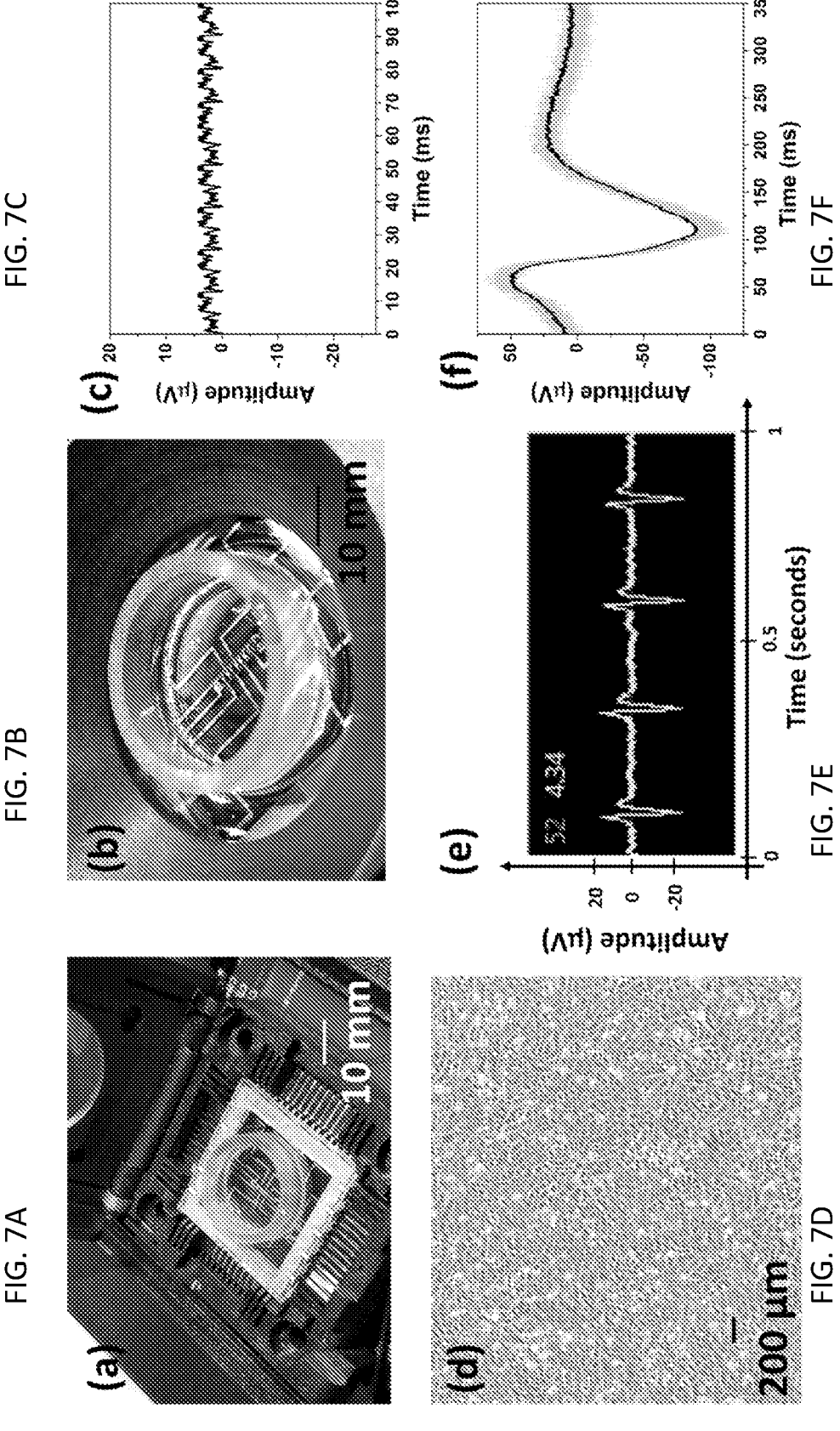
FIGS. 7A-7F: The packaged device connected to the commercial Axion Biosystems MUSE electronics interface.

FIG. 7 shows the fabricated device interfaced with the Axion BioSystem MUSE electronics amplifier [FIGS. 7 (a) and (b)]. The design was intended for intimate connectivity between the device and the amplifier system, and the results clearly illustrate this achievement. FIG. 7 (c) depicts peak to peak noise measured from the device and its connectivity to the MUSE system. It is observed to be ideal for neural and cardiac signal acquisition at a low value of 4.2 μV. FIG. 7 (d) shows the HL-1 cell line at 2 DIV (imaged in the culture flask). FIG. 7 (e) depicts a screen capture of classic extracellular cardiac action potentials of HL-1 cells, beating at about 5 Hz on the 3D MEA device. FIG. 7 (f) shows a superposition of 25 cardiac action potentials (average of 25 is highlighted). The beating activity demonstrates the device's biocompatibility and good electrophysiological interfacing capabilities of the 3D SS electrodes.

IV. Conclusions

In this paper, we report the microfabrication and assembly of 3D stainless steel MEAs on a glass substrate for optical probing of electrogenic cells. A technology was developed using laser micromachining, metallization, 3D printing, ink casting, PDMS insulation with materials having biological compatibility to adapt it as a tool for interrogation of 3D cell culture models. The orientation of the 3D microneedle electrodes measures an average of 89° with the horizontal for N=10 microneedles and was found consistent across multiple devices. Electrical Impedance Spectroscopy of the fully fabricated and assembled device produced a real impedance of 6.9 kΩ with phase of −12.3°@1 kHz (for the assembled device) and 13.3 kΩ with phase of −12.1°@1 kHz (for the packaged device). Both of these values are comparable to other reported values in literature. The packaged interconnect vias was additionally measured 3.99Ω for N=10 vias. The 3D MEA was further interfaced with commercial electronics amplification system and reported electrodes with an excellent noise of 4.2 μV. Lastly cardiac beats were recorded from an immortal mouse cardiac cell line (HL-1) at 2 DIV depicting an end to end design, fabrication, packaging and characterization of the device. Such a device can play a vital role in the burgeoning and rapidly growing "Organ-on-a-Chip" marketplace.

EXAMPLE 1 REFERENCES

1. Lodish, H.; Berk, A.; Zipursky, S. L.; Matsudaira, P.; Baltimore, D.; Darnell, J., Molecular cell biology 4th edition. *National Center for Biotechnology Information, Bookshelf* 2000.
2. Matthews, G. G., *Cellular physiology of nerve and muscle*. Wiley Online Library: 2003.
3. Jeong, S.; Kim, S.; Buonocore, J.; Park, J.; Welsh, C. J.; Li, J.; Han, A., A three-dimensional arrayed microfluidic blood—brain barrier model with integrated electrical sensor array. *IEEE Transactions on Biomedical Engineering* 2017, 65 (2), 431-439.
4. Mustapha, N.; Prado, J.; Margo, C.; Rouane, A. In *Bioimpedance spectroscopy of human blood at low frequency using coplanar microelectrodes,* 11th Mediterranean Conference on Medical and Biomedical Engineering and Computing 2007, Springer: 2007; pp 186-189.
5. Viswam, V.; Obien, M. E. J.; Franke, F.; Frey, U.; Hierlemann, A. R., Optimal electrode size for multi-scale extracellular-potential recording from neuronal assemblies. *Frontiers in neuroscience* 2019, 13, 385.
6. Kim, G.; Kim, K.; Lee, E.; An, T.; Choi, W.; Lim, G.; Shin, J., Recent progress on microelectrodes in neural interfaces. *Materials* 2018, 11 (10), 1995.
7. Hong, J. H.; Choi, J. H.; Kim, T. Y.; Lee, K. J., Spiral reentry waves in confluent layer of HL-1 cardiomyocyte cell lines. *Biochemical and biophysical research communications* 2008, 377 (4), 1269-1273.
8. Watt, F. M.; Huck, W. T., Role of the extracellular matrix in regulating stem cell fate. *Nature reviews Molecular cell biology* 2013, 14 (8), 467.
9. Azim, N.; Kundu, A.; Royse, M.; Sip, Y. Y. L.; Young, M.; Santra, S.; Zhai, L.; Rajaraman, S., Fabrication and Characterization of a 3D Printed, MicroElectrodes Platform With Functionalized Electrospun Nano-Scaffolds and Spin Coated 3D Insulation Towards Multi-Functional Biosystems. *Journal of Microelectromechanical Systems* 2019.
10. Bušek, D.; Mach, P. In *Study of glass transition temperature of electrically conductive adhesives,* 2012 IEEE 18th International Symposium for Design and Technology in Electronic Packaging (SIITME), IEEE: 2012; pp 143-146.
11. Sharma, A. D.; McCoy, L.; Jacobs, E.; Willey, H.; Behn, J. Q.; Nguyen, H.; Bolon, B.; Curley, J. L.; Moore, M. J., Engineering a 3D functional human peripheral nerve in vitro using the Nerve-on-a-Chip platform. *Scientific Reports* 2019, 9 (1), 8921.
12. Egert, U.; Meyer, T., Heart on a chip—extracellular multielectrode recordings from cardiac myocytes in vitro. In *Practical methods in cardiovascular research*, Springer: 2005; pp 432-453.
13. Kundu, A.; Ausaf, T.; Rajaraman, S. J. M., 3D Printing, Ink Casting and Micromachined Lamination (3D PICLμM): A Makerspace Approach to the Fabrication of Biological Microdevices. 2018, 9 (2), 85.
14. Azim, N.; Kundu, A.; Royse, M.; Sip, Y. Y. L.; Young, M.; Santra, S.; Zhai, L.; Rajaraman, S. J. J. o. M. S., Fabrication and Characterization of a 3D Printed, Micro-Electrodes Platform With Functionalized Electrospun Nano-Scaffolds and Spin Coated 3D Insulation Towards Multi-Functional Biosystems. 2019.
15. Kundu, A.; Nattoo, C.; Fremgen, S.; Springer, S.; Ausaf, T.; Rajaraman, S. J. R. a., Optimization of makerspace microfabrication techniques and materials for the realization of planar, 3D printed microelectrode arrays in under four days. 2019, 9 (16), 8949-8963.
16. Lacroix, C.; Bousmina, M.; Carreau, P.; Favis, B.; Michel, A., Properties of PETG/EVA blends: 1. Viscoelastic, morphological and interfacial properties. *Polymer* 1996, 37 (14), 2939-2947.
17. https://www.axionbiosystems.com
18. Claycomb, W. C.; Lanson, N. A.; Stallworth, B. S.; Egeland, D. B.; Delcarpio, J. B.; Bahinski, A.; Izzo, N. J., HL-1 cells: a cardiac muscle cell line that contracts and retains phenotypic characteristics of the adult cardiomyocyte. *Proc. Natl. Acad. Sci.* 1998, 95 (6), 2979-2984.
19. Harrington, D. A.; Van Den Driessche, P., Mechanism and equivalent circuits in electrochemical impedance spectroscopy. *Electrochimica Acta* 2011, 56 (23), 8005-8013.
20. Brug, G.; Van Den Eeden, A.; Sluyters-Rehbach, M.; Sluyters, J., The analysis of electrode impedances complicated by the presence of a constant phase element. *Journal of electroanalytical chemistry and interfacial electrochemistry* 1984, 176 (1-2), 275-295.
21. Kundu, A.; Nattoo, C.; Fremgen, S.; Springer, S.; Ausaf, T.; Rajaraman, S., Optimization of makerspace microfabrication techniques and materials for the realization of planar, 3D printed microelectrode arrays in under four days. *RSC Adv.* 2019, 9 (16), 8949-8963.
22. Guvanasen, G. S.; Guo, L.; Aguilar, R. J.; Cheek, A. L.; Shafor, C. S.; Rajaraman, S.; Nichols, T. R.; DeWeerth, S. P., A stretchable microneedle electrode array for stimulating and measuring intramuscular electromyographic activity. *IEEE Transactions on Neural Systems and Rehabilitation Engineering* 2016, 25 (9), 1440-1452.
23. Karnati, C.; Aguilar, R.; Arrowood, C.; Ross, J.; Rajaraman, S., Micromachining on and of transparent polymers for patterning electrodes and growing electrically active cells for biosensor applications. *Micromachines* 2017, 8 (8), 250.
24. Borkholder, D.; Bao, J.; Maluf, N.; Perl, E.; Kovacs, G., Microelectrode arrays for stimulation of neural slice preparations. *Journal of neuroscience methods* 1997, 77 (1), 61-66.
25. Borkholder, D. Cell based biosensors using microelectrodes. Stanford University, 1998.

Example 2: Fabrication and Characterization of 3D Microelectrode Arrays (3D MEAs) with "Edge-Wrapped" Metal Interconnects and 3D Printed Assembly Rigs for Simultaneous Optical and Electrical Probing of Nerve-On-a-Chip® Constructs

I. Introduction

Organ-on-a-chip models are becoming increasingly vital to model human tissues in vitro [1]. Microsystems to interrogate these tissue chips require multiple sensing modalities integrated on chip for simultaneous evaluation of these constructs. The requirement of 3D electrodes to interrogate a nervous system on a chip is clearly established [1]. Electrophysiological sensing is desirable using these 3D microelectrodes because it allows the measurement of clinically relevant parameters such as nerve conduction velocity (NCV) from in vitro model systems, such as a Nerve-on-a-Chip [2]. Enabling multimodal probing capabilities will ensure both electrophysiological and optical tracking of these cellular constructs as they mature. For optical probing, glass substrate MEAs are often a potential and desirable material solution, as the known optical clarity and extraordinary biocompatibility of glass is well documented. However, establishing front-back interconnects for such glass-based MEAs, can be challenging. To this end, development of new "edge-wrapped" trace routing techniques lends a scalable approach to the fabrication of 3D MEAs on optically transparent substrates. Assembly of 3D microelectrodes in the small footprint of the 3D MEA can be challenging and, toward this end, 3D printed assembly rigs can play a potential role.

In our previous work [3], we have demonstrated a packaging substrate-agnostic 3D MEA platform. In this work, we report device development strategies for a custom microneedle (μN) based "key-shaped array" 3D MEA; a unique linear 3D electrode architecture which is designed to stimulate and record down the length of an engineered neuronal axonal fiber tract, while still maintaining optical clarity. The method detailed here, entails the creation of a unique construct, which is assembled using both additive and selective technologies in a "Makerspace Microfabrication" process flow. The resulting device is integrated with a unique Nerve-on-a-Chip® [2] 3D nerve model atop the array. Prior to the nerve-chip integration, microelectrode characterization ensures proper conditions for electrical cellular interrogation. As a result, mechanical and electrical data from the 3D MEA, growth and viability of primary rat DRG cells defined in the Nerve-on-a-Chip® and grown for 28 DIV are successfully demonstrated.

II. Materials

Figures 8A, 8B, 8C, 8D, 8E:
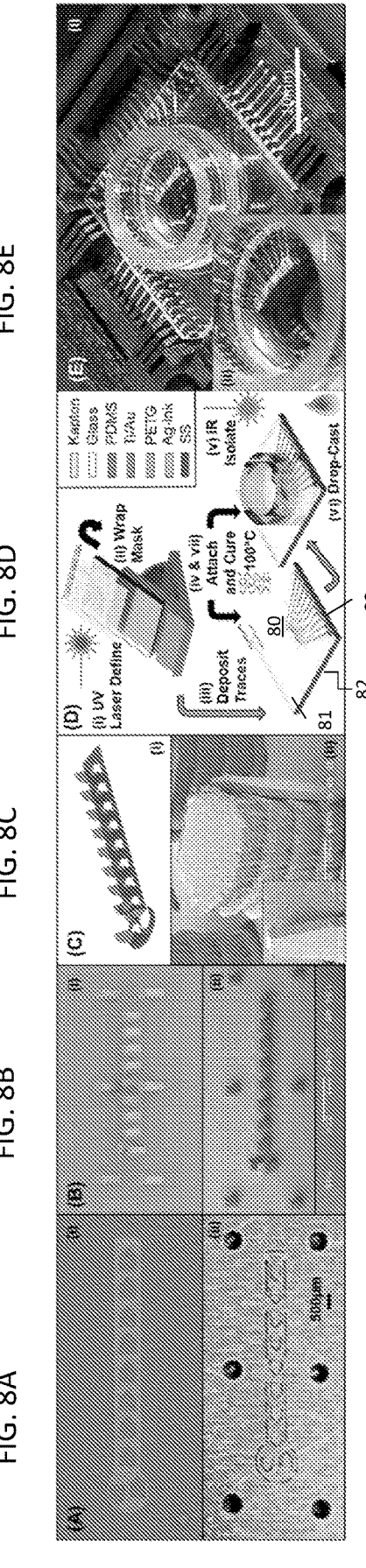
FIG. 8A-8E: Process flow for the 3D MEA, illustrating design to device translation.
Figures 9A, 9B:
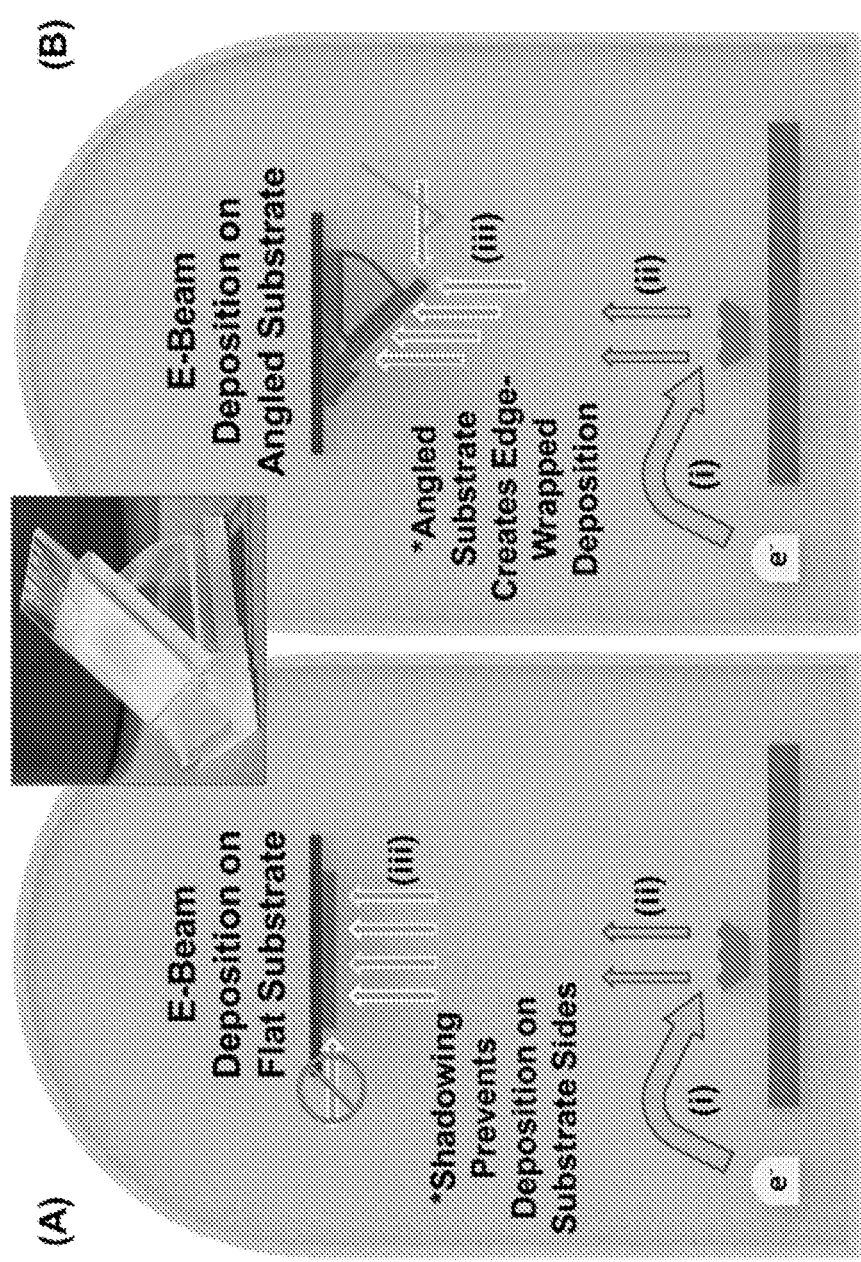
FIG. 9A-9B: Schematic representation of Electron-Beam deposition inside the bell-jar. (A) Schematic of e-beam deposition with substrate flat (traditional). (B) Schematic of e-beam deposition with substrate placed on the 3D printed angled deposition platform. (A; iii) The flat substrate receives the deposition material only on the bottom surface and cannot be coated on the side due to shadowing. (B; iii) The angled substrate is able to be deposited on both the flat surface and the edge. Another deposition to coat the backside completes the process. The inset shows an optical image of the substrate, placed on the 3D-printed angled deposition rig, with the deposited Ti/Au traces.

Stainless Steel (SS) substrates of 25 μm thickness were laser micromachined into a 10-microneedle, key-shaped design (FIG. 8A; 800 μm circle and 5 mm linear array). 2D to 3D transition guides for the micromachined SS were designed in Solidworks CAD software, printed on an Asiga DLP 3D printer, washed in 70% IPA and UV cured for 30 minutes (FIG. 8B). The key-shaped SS array was subsequently acid pickled and pressed onto the transition guide, to facilitate the final 3D MEA conformation (FIG. 8C). Separately, 1.5 mm thick glass slides were machined and sanded to a 24×24 mm size. These slides were cleaned in a base bath (10% w/v; KOH/H2O+IPA) for 24 hours, and then rinsed in a DI water bath. A custom shadow mask with "edge-wrapped" metal trace pattern was laser micromachined from 12.5 μm Kapton® tape and applied to the cleaned glass slides (FIG. 8D). FIG. 8D shows the substrate 80 that has a top surface 81, a bottom surface 82 on the opposite side to the top surface 81, and an edge surface 83. A multi-chip, angled deposition construct was designed, and 3D printed using the DLP process discussed. The aligned glass slide with the shadow mask was placed on the construct and the "edge-wrapped" interconnects were defined (100 nm Ti/400 nm Au) using electron-beam evaporation (FIG. 9A-B). Conductive Agepoxy (12.5 μm thick) was then applied selectively to the central electrode pads through the same mask. The transitioned 3D MEA was aligned and placed atop the epoxy and cured at 60° C. overnight. The MEA was subsequently singulated using IR laser micromachining, insulated using PDMS, and contained with a culture well (FIG. 8D). Impedance spectroscopy and RMS noise measurements were performed on the BODE 100 and Axion BioSystems MUSE electrophysiological measurement systems (FIG. 8E) respectively.

A Nerve-on-a-Chip® hydrogel construct was fabricated on the 3D MEA using photolithography techniques as previously reported [2]. A single explanted rat DRG (embryonic day 15) was inserted into a Nerve-on-a-Chip® construct comprising a cell-permissive inner gel with an outer cell-restrictive hydrogel to facilitate dense, 3D axonal growth surrounding the 3D MEA needle electrodes. Following 28 DIV culture, the nerve tissue was imaged using brightfield microscopy, and stained with Calcein AM, a live cell marker, for immunofluorescence microscopy on a Nikon AZ100 system.

III. Results and Discussions

Figures 10A, 10B, 10C:
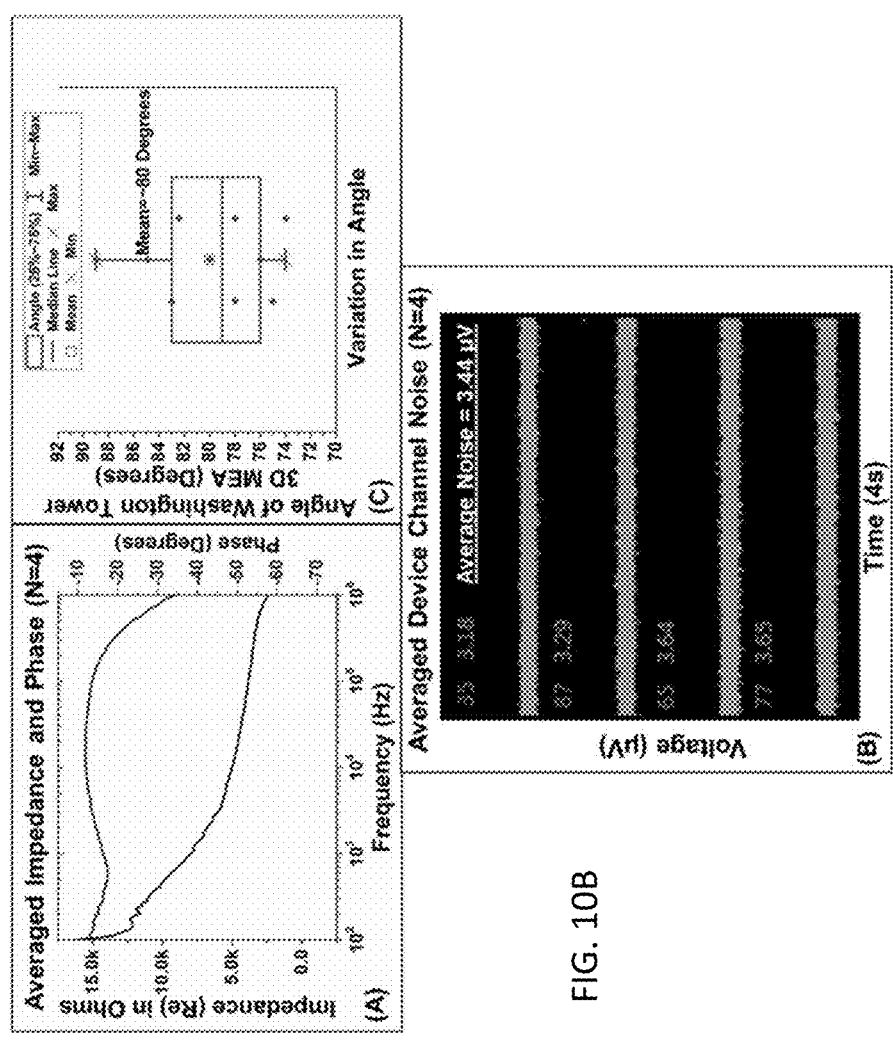
FIG. 10A-10C: Characterization of the 3D MEA.

FIG. 10 reports electrical and mechanical characterization of the 3D MEA. Full spectrum impedance and phase performance (FIG. 10A; N=4) demonstrate physiologically relevant 1 kHz values of 7.5 kΩ and −20° respectively, comparable to literature values [4]. The average RMS noise for these devices (FIG. 10B; N=4) was 3.44 μV, similarly comparable to literature values [5]. The 3D printed transition rig demonstrated reliable performance with a mean angle of 80° (N=10; FIG. 10C).

Figures 11A, 11B:
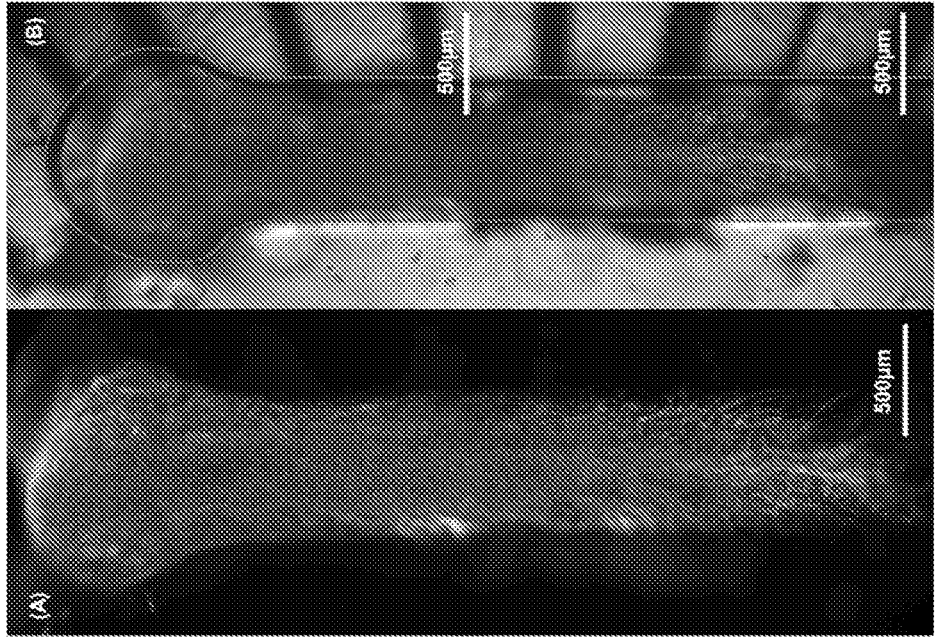
FIG. 11A-11B: Growth of rat DRGs at 28 DIV atop the 3D MEA.

Rat DRG cells were cultured on 3D MEA Nerve-on-a-Chip® devices (N=3) for 28 days to permit robust axon extension and Schwann cell proliferation and myelination. Calcein AM imaging (FIG. 11) showed dense axonal growth colocalized with the 3D microelectrodes on all 3D MEA samples, demonstrating long-term biocompatibility. Dense cell proliferation and migration was observed in the channel region proximal to the MEA circular region of the key shape- (FIG. 11B), while axonal outgrowth was clearly seen in the channel region.

By transposing the Calcein AM staining on the brightfield microscopy imaging (FIG. 11B), the robustness of the culture at 28 DIV, as well as axonal growth are clearly illustrated. Future work will be focused on detailing the functional electrophysiological recordings with the linear region of the 3D MEA key-shaped architecture.

IV. Conclusions

Organ-on-a-chip models are becoming a necessity for in vitro tissue culture and characterization[1, 3], and new and intricate methods for simultaneous optical and electrical interfacing with these models will become vitally important for such organ-on-a-chip strategies. In this Example 2 a new microfabrication and assembly strategy for a 3D MEA Nerve-on-a-Chip® interface, which centered around a custom MEA key-shaped design, built on an optically transparent glass substrate is demonstrated. In order to deliver electrical contacts to the bottom-side of the chip, an innovative "edge-wrapped" metal interconnects technique was developed using both a mask-wrapping technique paired with a custom angled deposition rig for uniform e-beam evaporated trace definition. Subsequently electrical impedance and RMS noise characterization of the devices were performed, demonstrating the suitability of this platform for in vitro neural electrophysiology. Lastly, biocompatibility and growth directionality of a Nerve-on-a-Chip® platform was assessed using fluorescent and brightfield microscopy at 28 DIV.

Such "Makerspace Microfabrication" strategies lend immense flexibility to development of analytical tools and will open avenues for new future iterations. Ongoing and future works include the functional recording of the DRG population, and investigation of drug/toxin responses.

EXAMPLE 2 REFERENCES

[1] K. Pollard et al., "Neural Microphysiological Systems for In Vitro Modeling of Peripheral Nervous System Disorders," Future Medicine, 2(2), (2019).
[2] A. D. Sharma et al., "Engineering a 3D Functional Human Peripheral Nerve In Vitro using the Nerve-on-a-Chip Platform," Sci Rep, 9, 8921, (2019).
[3] C. Didier et al., "Facile, Packaging Substrate-Agnostic, Microfabrication and Assembly of Scalable 3D Metal Microelectrode Arrays for In Vitro Organ-on-a-Chip and Cellular Disease Modeling," IEEE Transducers Conference, pp. 1686-1689, (2019).
[4] D. Borkholder, "Cell-Based Biosensors using Microelectrodes," Stanford Univ. Ph.D. Thesis, (1999).
[5] N. Azim et al., "Precision Plating of Human Electrogenic Cells on Microelectrodes Enhanced with Precision Electrodeposited Nano-Porous Platinum for Cell-Based Biosensing Applications," IEEE JMEMS, 28 (1), pp. 50-62, (2019).

What is claimed is:

1. A method of making a three-dimensional microelectrode array (3D MEA) comprising;

forming a plurality of cut-outs onto a planar conductive substrate;

transitioning material at the plurality of the cut-outs such that a plurality of microneedles extend orthogonally to the planar conductive substrate;

cutting the planar conductor substrate to release the plurality of microneedles from the planar conductive sheet to produce a released plurality of microneedles; and securing the released plurality of microneedles to a transparent planar substrate comprising a top surface, a bottom surface and an edge surface disposed on a side of the transparent planar substrate and between the top and bottom surfaces;

wherein one or more conductive traces have been deposited on both the edge surface and the bottom or top surface of the transparent planar substrate, or both, and wherein the released plurality of microneedles is secured suprajacent to the conducted traces such that at least one microneedle of the plurality of microneedles and at least one conductive trace of the one or more conductive traces are conductively connected.

2. The method of claim 1, wherein the planar conductive substrate is comprised of metal, polymer-metal composite, conductive silicon composites, or conductive glass.

3. The method of claim 2, wherein the metal comprises stainless steel, titanium, zinc, magnesium nitinol, vanadium or combinations and alloys thereof.

4. The method of claim 1, wherein the transparent planar substrate comprises glass or transparent polymer.

5. The method of claim 1, wherein the microneedles are at a greater than 60, 70 or 80 degree angle respective to the planar conductive sheet.

6. The method of claim 5, wherein the microneedles are at a greater than 80 degree angle.

7. The method of claim 1, further comprising depositing an insulation layer onto the plurality of microneedles.

8. The method of claim 7, wherein the insulation layer comprises parylene, poly-di-methyl-siloxane (PDMS), SU-8, silicon dioxide, polyimide, polyurethane, poly lactic acid, poly glycolic acid, poly lactic glycolic acid, poly vinyl alcohol, polystyrene, poly ethylene glycol, poly ethylene terephthalate, poly ethylene terephthalate glycol, poly ethylene naphthalate, or a combination thereof and deposited such that a portion of the plurality of microelectrodes is exposed and a portion of the microelectrodes is covered by the insulation layer.

9. The method of claim 7, wherein the insulation layer is deposed by confined precision drop casting.

10. The method of claim 1, further comprising placing cells onto the plurality of microneedles following the securing step.

11. The method of claim 10, wherein the cells comprise electrogenic cells.

12. The method of claim 11, further comprising detecting electrophysiological signals from the electrogenic cells.

13. The method of claim 1, further comprising, before securing the released plurality of microneedles to the transparent planar substrate body, applying a mask to the transparent planar substrate body such that the mask covers at least a portion of either the top surface or bottom surface and the edge surface, the mask comprising at least one opening; and depositing a conductive material onto the transparent planar substrate body through the at least one opening.

14. The method of claim 13, wherein the depositing is conducted by E-beam deposition, resistive deposition, laser deposition, screen printing, or electroplating.

15. The method of claim 13, wherein the transparent planar substrate body with mask applied is held at an angle during depositing such that conductive material is deposited to the edge surface.

16. The method of claim 15, wherein the transparent planar substrate body is held at an angle by an angled deposition rig, the deposition rig comprising a base portion and a bracket portion secured orthogonally to the base portion.

17. A 3D MEA produced by the method of claim 1.

18. The method of claim 1, wherein the released plurality of 3D microneedles comprise a first portion comprising a first set of 3D microneedles and having a first width dimension and a first length dimension, and a second portion comprising a second set of 3D microneedles and having a second width dimension and a second length dimension, wherein the second width dimension is larger than the first width dimension and the first length dimension is larger than the second length dimension, and, optionally, further comprising conductively isolating the plurality of 3D microneedles from each other.

19. The method of claim 18, further comprising:

forming a microengineered microphysiological system by placing neuronal cells over at least a portion of the second portion or seeding tissue explants over at least a portion of the second portion;

growing axons over at least a portion of the first portion; and performing real-time, detection of one or more bioelectrical signals in the microengineered physiological system.

20. The method of claim 5, wherein the angle is about 60-90 degrees, about 70-90 degrees or about 80-90 degrees.

* * * * *